(12) United States Patent
Hayter et al.

(10) Patent No.: US 8,718,965 B2
(45) Date of Patent: *May 6, 2014

(54) METHOD AND APPARATUS FOR PROVIDING ANALYTE MONITORING SYSTEM CALIBRATION ACCURACY

(71) Applicant: Abbott Diabetes Care Inc., Alameda, CA (US)

(72) Inventors: Gary Alan Hayter, Oakland, CA (US); Erwin Satrya Budiman, Fremont, CA (US)

(73) Assignee: Abbott Diabetes Care Inc., Alameda, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/925,691

(22) Filed: Jun. 24, 2013

(65) Prior Publication Data

US 2013/0282322 A1    Oct. 24, 2013

Related U.S. Application Data

(63) Continuation of application No. 12/848,075, filed on Jul. 30, 2010, now Pat. No. 8,478,557.

(60) Provisional application No. 61/230,686, filed on Jul. 31, 2009.

(51) Int. Cl.
*G01C 19/00* (2013.01)
*A61B 5/00* (2006.01)

(52) U.S. Cl.
USPC ......................................... 702/104; 600/365

(58) Field of Classification Search
USPC ......... 702/104, 19, 22–23, 30, 33, 81, 84–85, 702/127, 176–178, 182–183, 189; 600/300, 600/309, 365; 604/48, 65–66, 500, 504, 604/890.1
See application file for complete search history.

(56) References Cited

U.S. PATENT DOCUMENTS

| | | |
|---|---|---|
| 3,581,062 A | 5/1971 | Aston |
| 3,926,760 A | 12/1975 | Allen et al. |
| 3,949,388 A | 4/1976 | Fuller |
| 4,036,749 A | 7/1977 | Anderson |
| 4,055,175 A | 10/1977 | Clemens et al. |
| 4,129,128 A | 12/1978 | McFarlane |
| 4,245,634 A | 1/1981 | Albisser et al. |
| 4,327,725 A | 5/1982 | Cortese et al. |
| 4,344,438 A | 8/1982 | Schultz |

(Continued)

FOREIGN PATENT DOCUMENTS

| | | |
|---|---|---|
| AU | 2003/259741 | 2/2004 |
| CA | 2495648 | 2/2004 |

(Continued)

OTHER PUBLICATIONS

Armour, J. C., et al., "Application of Chronic Intravascular Blood Glucose Sensor in Dogs", *Diabetes*, vol. 39, 1990, pp. 1519-1526.

(Continued)

*Primary Examiner* — Toan Le
(74) *Attorney, Agent, or Firm* — Jackson & Co., LLP

(57) ABSTRACT

Methods, system and devices for providing improved calibration accuracy of continuous glucose monitoring system based on insulin delivery information are provided.

20 Claims, 13 Drawing Sheets

(56) References Cited

U.S. PATENT DOCUMENTS

| | | |
|---|---|---|
| 4,349,728 A | 9/1982 | Phillips et al. |
| 4,373,527 A | 2/1983 | Fischell |
| 4,392,849 A | 7/1983 | Petre et al. |
| 4,425,920 A | 1/1984 | Bourland et al. |
| 4,431,004 A | 2/1984 | Bessman et al. |
| 4,441,968 A | 4/1984 | Emmer et al. |
| 4,464,170 A | 8/1984 | Clemens et al. |
| 4,478,976 A | 10/1984 | Goertz et al. |
| 4,494,950 A | 1/1985 | Fischell |
| 4,509,531 A | 4/1985 | Ward |
| 4,527,240 A | 7/1985 | Kvitash |
| 4,538,616 A | 9/1985 | Rogoff |
| 4,619,793 A | 10/1986 | Lee |
| 4,671,288 A | 6/1987 | Gough |
| 4,703,756 A | 11/1987 | Gough et al. |
| 4,731,726 A | 3/1988 | Allen, III |
| 4,749,985 A | 6/1988 | Corsberg |
| 4,757,022 A | 7/1988 | Shults et al. |
| 4,777,953 A | 10/1988 | Ash et al. |
| 4,779,618 A | 10/1988 | Mund et al. |
| 4,847,785 A | 7/1989 | Stephens |
| 4,854,322 A | 8/1989 | Ash et al. |
| 4,871,351 A | 10/1989 | Feingold |
| 4,890,620 A | 1/1990 | Gough |
| 4,925,268 A | 5/1990 | Iyer et al. |
| 4,953,552 A | 9/1990 | DeMarzo |
| 4,986,271 A | 1/1991 | Wilkins |
| 4,995,402 A | 2/1991 | Smith et al. |
| 5,000,180 A | 3/1991 | Kuypers et al. |
| 5,002,054 A | 3/1991 | Ash et al. |
| 5,019,974 A | 5/1991 | Beckers |
| 5,050,612 A | 9/1991 | Matsumura |
| 5,051,688 A | 9/1991 | Murase et al. |
| 5,055,171 A | 10/1991 | Peck |
| 5,068,536 A | 11/1991 | Rosenthal |
| 5,082,550 A | 1/1992 | Rishpon et al. |
| 5,106,365 A | 4/1992 | Hernandez |
| 5,122,925 A | 6/1992 | Inpyn |
| 5,135,004 A | 8/1992 | Adams et al. |
| 5,165,407 A | 11/1992 | Wilson et al. |
| 5,202,261 A | 4/1993 | Musho et al. |
| 5,210,778 A | 5/1993 | Massart |
| 5,228,449 A | 7/1993 | Christ et al. |
| 5,231,988 A | 8/1993 | Wernicke et al. |
| 5,246,867 A | 9/1993 | Lakowicz et al. |
| 5,251,126 A | 10/1993 | Kahn et al. |
| 5,262,035 A | 11/1993 | Gregg et al. |
| 5,262,305 A | 11/1993 | Heller et al. |
| 5,264,104 A | 11/1993 | Gregg et al. |
| 5,264,105 A | 11/1993 | Gregg et al. |
| 5,279,294 A | 1/1994 | Anderson et al. |
| 5,284,425 A | 2/1994 | Holtermann et al. |
| 5,285,792 A | 2/1994 | Sjoquist et al. |
| 5,293,877 A | 3/1994 | O'Hara et al. |
| 5,299,571 A | 4/1994 | Mastrototaro |
| 5,320,725 A | 6/1994 | Gregg et al. |
| 5,322,063 A | 6/1994 | Allen et al. |
| 5,330,634 A | 7/1994 | Wong et al. |
| 5,340,722 A | 8/1994 | Wolfbeis et al. |
| 5,342,789 A | 8/1994 | Chick et al. |
| 5,356,786 A | 10/1994 | Heller et al. |
| 5,360,404 A | 11/1994 | Novacek et al. |
| 5,372,427 A | 12/1994 | Padovani et al. |
| 5,379,238 A | 1/1995 | Stark |
| 5,384,547 A | 1/1995 | Lynk et al. |
| 5,390,671 A | 2/1995 | Lord et al. |
| 5,391,250 A | 2/1995 | Cheney, II et al. |
| 5,408,999 A | 4/1995 | Singh et al. |
| 5,410,326 A | 4/1995 | Goldstein |
| 5,411,647 A | 5/1995 | Johnson et al. |
| 5,425,868 A | 6/1995 | Pedersen |
| 5,429,602 A | 7/1995 | Hauser |
| 5,431,160 A | 7/1995 | Wilkins |
| 5,431,921 A | 7/1995 | Thombre |
| 5,462,645 A | 10/1995 | Albery et al. |
| 5,497,772 A | 3/1996 | Schulman et al. |
| 5,505,828 A | 4/1996 | Wong et al. |
| 5,507,288 A | 4/1996 | Bocker et al. |
| 5,509,410 A | 4/1996 | Hill et al. |
| 5,514,718 A | 5/1996 | Lewis et al. |
| 5,531,878 A | 7/1996 | Vadgama et al. |
| 5,552,997 A | 9/1996 | Massart |
| 5,568,400 A | 10/1996 | Stark et al. |
| 5,568,806 A | 10/1996 | Cheney, II et al. |
| 5,569,186 A | 10/1996 | Lord et al. |
| 5,582,184 A | 12/1996 | Erickson et al. |
| 5,586,553 A | 12/1996 | Halili et al. |
| 5,593,852 A | 1/1997 | Heller et al. |
| 5,609,575 A | 3/1997 | Larson et al. |
| 5,628,310 A | 5/1997 | Rao et al. |
| 5,628,324 A | 5/1997 | Sarbach |
| 5,653,239 A | 8/1997 | Pompei et al. |
| 5,660,163 A | 8/1997 | Schulman et al. |
| 5,665,222 A | 9/1997 | Heller et al. |
| 5,711,001 A | 1/1998 | Bussan et al. |
| 5,711,861 A | 1/1998 | Ward et al. |
| 5,733,259 A | 3/1998 | Valcke et al. |
| 5,738,220 A | 4/1998 | Geszler |
| 5,748,103 A | 5/1998 | Flach et al. |
| 5,772,586 A | 6/1998 | Heinonen et al. |
| 5,791,344 A | 8/1998 | Schulman et al. |
| 5,833,603 A | 11/1998 | Kovacs et al. |
| 5,842,189 A | 11/1998 | Keeler et al. |
| 5,899,855 A | 5/1999 | Brown |
| 5,925,021 A | 7/1999 | Castellano et al. |
| 5,935,224 A | 8/1999 | Svancarek et al. |
| 5,942,979 A | 8/1999 | Luppino |
| 5,957,854 A | 9/1999 | Besson et al. |
| 5,964,993 A | 10/1999 | Blubaugh, Jr. et al. |
| 5,965,380 A | 10/1999 | Heller et al. |
| 5,971,922 A | 10/1999 | Arita et al. |
| 5,980,708 A | 11/1999 | Champagne et al. |
| 5,995,860 A | 11/1999 | Sun et al. |
| 6,001,067 A | 12/1999 | Shults et al. |
| 6,024,699 A | 2/2000 | Surwit et al. |
| 6,028,413 A | 2/2000 | Brockmann |
| 6,049,727 A | 4/2000 | Crothall |
| 6,052,565 A | 4/2000 | Ishikura et al. |
| 6,066,243 A | 5/2000 | Anderson et al. |
| 6,083,710 A | 7/2000 | Heller et al. |
| 6,088,608 A | 7/2000 | Schulman et al. |
| 6,091,976 A | 7/2000 | Pfeiffer et al. |
| 6,093,172 A | 7/2000 | Funderburk et al. |
| 6,096,364 A | 8/2000 | Bok et al. |
| 6,103,033 A | 8/2000 | Say et al. |
| 6,117,290 A | 9/2000 | Say et al. |
| 6,119,028 A | 9/2000 | Schulman et al. |
| 6,120,676 A | 9/2000 | Heller et al. |
| 6,121,009 A | 9/2000 | Heller et al. |
| 6,121,611 A | 9/2000 | Lindsay et al. |
| 6,122,351 A | 9/2000 | Schlueter, Jr. et al. |
| 6,134,461 A | 10/2000 | Say et al. |
| 6,143,164 A | 11/2000 | Heller et al. |
| 6,162,611 A | 12/2000 | Heller et al. |
| 6,175,752 B1 | 1/2001 | Say et al. |
| 6,200,265 B1 | 3/2001 | Walsh et al. |
| 6,212,416 B1 | 4/2001 | Ward et al. |
| 6,219,574 B1 | 4/2001 | Cormier et al. |
| 6,233,471 B1 | 5/2001 | Berner et al. |
| 6,248,067 B1 | 6/2001 | Causey, III et al. |
| 6,275,717 B1 | 8/2001 | Gross et al. |
| 6,284,478 B1 | 9/2001 | Heller et al. |
| 6,293,925 B1 | 9/2001 | Safabash et al. |
| 6,295,506 B1 | 9/2001 | Heinonen et al. |
| 6,299,347 B1 | 10/2001 | Pompei |
| 6,306,104 B1 | 10/2001 | Cunningham et al. |
| 6,309,884 B1 | 10/2001 | Cooper et al. |
| 6,329,161 B1 | 12/2001 | Heller et al. |
| 6,359,270 B1 | 3/2002 | Bridson |
| 6,360,888 B1 | 3/2002 | McIvor et al. |
| 6,366,794 B1 | 4/2002 | Moussy et al. |
| 6,377,828 B1 | 4/2002 | Chaiken et al. |
| 6,379,301 B1 | 4/2002 | Worthington et al. |
| 6,424,847 B1 | 7/2002 | Mastrototaro et al. |

(56) References Cited

U.S. PATENT DOCUMENTS

| | | |
|---|---|---|
| 6,427,088 B1 | 7/2002 | Bowman, IV et al. |
| 6,440,068 B1 | 8/2002 | Brown et al. |
| 6,471,689 B1 | 10/2002 | Joseph et al. |
| 6,478,736 B1 | 11/2002 | Mault |
| 6,484,046 B1 | 11/2002 | Say et al. |
| 6,493,069 B1 | 12/2002 | Nagashimada et al. |
| 6,498,043 B1 | 12/2002 | Schulman et al. |
| 6,514,718 B2 | 2/2003 | Heller et al. |
| 6,544,212 B2 | 4/2003 | Galley et al. |
| 6,546,268 B1 | 4/2003 | Ishikawa et al. |
| 6,551,494 B1 | 4/2003 | Heller et al. |
| 6,554,798 B1 | 4/2003 | Mann et al. |
| 6,558,320 B1 | 5/2003 | Causey, III et al. |
| 6,558,321 B1 | 5/2003 | Burd et al. |
| 6,558,351 B1 | 5/2003 | Steil et al. |
| 6,560,471 B1 | 5/2003 | Heller et al. |
| 6,561,978 B1 | 5/2003 | Conn et al. |
| 6,562,001 B2 | 5/2003 | Lebel et al. |
| 6,564,105 B2 | 5/2003 | Starkweather et al. |
| 6,565,509 B1 | 5/2003 | Say et al. |
| 6,571,128 B2 | 5/2003 | Lebel et al. |
| 6,572,545 B2 | 6/2003 | Knobbe et al. |
| 6,576,101 B1 | 6/2003 | Heller et al. |
| 6,577,899 B2 | 6/2003 | Lebel et al. |
| 6,579,690 B1 | 6/2003 | Bonnecaze et al. |
| 6,585,644 B2 | 7/2003 | Lebel et al. |
| 6,591,125 B1 | 7/2003 | Buse et al. |
| 6,595,919 B2 | 7/2003 | Berner et al. |
| 6,605,200 B1 | 8/2003 | Mao et al. |
| 6,605,201 B1 | 8/2003 | Mao et al. |
| 6,607,509 B2 | 8/2003 | Bobroff et al. |
| 6,610,012 B2 | 8/2003 | Mault |
| 6,633,772 B2 | 10/2003 | Ford et al. |
| 6,635,014 B2 | 10/2003 | Starkweather et al. |
| 6,641,533 B2 | 11/2003 | Causey, III et al. |
| 6,648,821 B2 | 11/2003 | Lebel et al. |
| 6,654,625 B1 | 11/2003 | Say et al. |
| 6,656,114 B1 | 12/2003 | Poulsen et al. |
| 6,658,396 B1 | 12/2003 | Tang et al. |
| 6,659,948 B2 | 12/2003 | Lebel et al. |
| 6,668,196 B1 | 12/2003 | Villegas et al. |
| 6,675,030 B2 | 1/2004 | Ciuczak et al. |
| 6,676,816 B2 | 1/2004 | Mao et al. |
| 6,687,546 B2 | 2/2004 | Lebel et al. |
| 6,689,056 B1 | 2/2004 | Kilcoyne et al. |
| 6,694,191 B2 | 2/2004 | Starkweather et al. |
| 6,695,860 B1 | 2/2004 | Ward et al. |
| 6,698,269 B2 | 3/2004 | Baber et al. |
| 6,702,857 B2 | 3/2004 | Brauker et al. |
| 6,733,446 B2 | 5/2004 | Lebel et al. |
| 6,740,075 B2 | 5/2004 | Lebel et al. |
| 6,740,518 B1 | 5/2004 | Duong et al. |
| 6,741,877 B1 | 5/2004 | Shults et al. |
| 6,746,582 B2 | 6/2004 | Heller et al. |
| 6,758,810 B2 | 7/2004 | Lebel et al. |
| 6,770,030 B1 | 8/2004 | Schaupp et al. |
| 6,789,195 B1 | 9/2004 | Prihoda et al. |
| 6,790,178 B1 | 9/2004 | Mault et al. |
| 6,809,653 B1 | 10/2004 | Mann et al. |
| 6,810,290 B2 | 10/2004 | Lebel et al. |
| 6,811,533 B2 | 11/2004 | Lebel et al. |
| 6,811,534 B2 | 11/2004 | Bowman, IV et al. |
| 6,813,519 B2 | 11/2004 | Lebel et al. |
| 6,862,465 B2 | 3/2005 | Shults et al. |
| 6,865,407 B2 | 3/2005 | Kimball et al. |
| 6,873,268 B2 | 3/2005 | Lebel et al. |
| 6,881,551 B2 | 4/2005 | Heller et al. |
| 6,882,940 B2 | 4/2005 | Potts et al. |
| 6,892,085 B2 | 5/2005 | McIvor et al. |
| 6,895,263 B2 | 5/2005 | Shin et al. |
| 6,895,265 B2 | 5/2005 | Silver |
| 6,923,763 B1 | 8/2005 | Kovatchev et al. |
| 6,931,327 B2 | 8/2005 | Goode, Jr. et al. |
| 6,932,894 B2 | 8/2005 | Mao et al. |
| 6,936,006 B2 | 8/2005 | Sabra |
| 6,950,708 B2 | 9/2005 | Bowman, IV et al. |
| 6,958,705 B2 | 10/2005 | Lebel et al. |
| 6,968,294 B2 | 11/2005 | Gutta et al. |
| 6,971,274 B2 | 12/2005 | Olin |
| 6,974,437 B2 | 12/2005 | Lebel et al. |
| 6,983,176 B2 | 1/2006 | Gardner et al. |
| 6,990,366 B2 | 1/2006 | Say et al. |
| 6,997,907 B2 | 2/2006 | Safabash et al. |
| 6,998,247 B2 | 2/2006 | Monfre et al. |
| 7,003,336 B2 | 2/2006 | Holker et al. |
| 7,003,340 B2 | 2/2006 | Say et al. |
| 7,003,341 B2 | 2/2006 | Say et al. |
| 7,016,713 B2 | 3/2006 | Gardner et al. |
| 7,022,072 B2 | 4/2006 | Fox et al. |
| 7,024,245 B2 | 4/2006 | Lebel et al. |
| 7,025,425 B2 | 4/2006 | Kovatchev et al. |
| 7,027,848 B2 | 4/2006 | Robinson et al. |
| 7,027,931 B1 | 4/2006 | Jones et al. |
| 7,029,444 B2 | 4/2006 | Shin et al. |
| 7,041,068 B2 | 5/2006 | Freeman et al. |
| 7,052,483 B2 | 5/2006 | Wojcik |
| 7,056,302 B2 | 6/2006 | Douglas |
| 7,074,307 B2 | 7/2006 | Simpson et al. |
| 7,081,195 B2 | 7/2006 | Simpson et al. |
| 7,092,891 B2 | 8/2006 | Maus et al. |
| 7,098,803 B2 | 8/2006 | Mann et al. |
| 7,108,778 B2 | 9/2006 | Simpson et al. |
| 7,110,803 B2 | 9/2006 | Shults et al. |
| 7,113,821 B1 | 9/2006 | Sun et al. |
| 7,118,667 B2 | 10/2006 | Lee |
| 7,134,999 B2 | 11/2006 | Brauker et al. |
| 7,136,689 B2 | 11/2006 | Shults et al. |
| 7,153,265 B2 | 12/2006 | Vachon |
| 7,155,290 B2 | 12/2006 | Von Arx et al. |
| 7,171,274 B2 | 1/2007 | Starkweather et al. |
| 7,174,199 B2 | 2/2007 | Berner et al. |
| 7,190,988 B2 | 3/2007 | Say et al. |
| 7,192,450 B2 | 3/2007 | Brauker et al. |
| 7,198,606 B2 | 4/2007 | Boecker et al. |
| 7,207,974 B2 | 4/2007 | Safabash et al. |
| 7,225,535 B2 | 6/2007 | Feldman et al. |
| 7,226,442 B2 | 6/2007 | Sheppard et al. |
| 7,226,978 B2 | 6/2007 | Tapsak et al. |
| 7,258,673 B2 | 8/2007 | Racchini et al. |
| 7,267,665 B2 | 9/2007 | Steil et al. |
| 7,276,029 B2 | 10/2007 | Goode, Jr. et al. |
| 7,278,983 B2 | 10/2007 | Ireland et al. |
| 7,286,894 B1 | 10/2007 | Grant et al. |
| 7,299,082 B2 | 11/2007 | Feldman et al. |
| 7,310,544 B2 | 12/2007 | Brister et al. |
| 7,317,938 B2 | 1/2008 | Lorenz et al. |
| 7,335,294 B2 | 2/2008 | Heller et al. |
| 7,354,420 B2 | 4/2008 | Steil et al. |
| 7,364,592 B2 | 4/2008 | Carr-Brendel et al. |
| 7,366,556 B2 | 4/2008 | Brister et al. |
| 7,379,765 B2 | 5/2008 | Petisce et al. |
| 7,402,153 B2 | 7/2008 | Steil et al. |
| 7,404,796 B2 | 7/2008 | Ginsberg |
| 7,424,318 B2 | 9/2008 | Brister et al. |
| 7,460,898 B2 | 12/2008 | Brister et al. |
| 7,467,003 B2 | 12/2008 | Brister et al. |
| 7,471,972 B2 | 12/2008 | Rhodes et al. |
| 7,474,992 B2 | 1/2009 | Ariyur |
| 7,492,254 B2 | 2/2009 | Bandy et al. |
| 7,494,465 B2 | 2/2009 | Brister et al. |
| 7,497,827 B2 | 3/2009 | Brister et al. |
| 7,519,408 B2 | 4/2009 | Rasdal et al. |
| 7,547,281 B2 | 6/2009 | Hayes et al. |
| 7,569,030 B2 | 8/2009 | Lebel et al. |
| 7,583,990 B2 | 9/2009 | Goode, Jr. et al. |
| 7,591,801 B2 | 9/2009 | Brauker et al. |
| 7,599,726 B2 | 10/2009 | Goode, Jr. et al. |
| 7,613,491 B2 | 11/2009 | Boock et al. |
| 7,615,007 B2 | 11/2009 | Shults et al. |
| 7,618,369 B2 | 11/2009 | Hayter et al. |
| 7,630,748 B2 | 12/2009 | Budiman |
| 7,632,228 B2 | 12/2009 | Brauker et al. |
| 7,637,868 B2 | 12/2009 | Saint et al. |
| 7,640,048 B2 | 12/2009 | Dobbles et al. |

(56) References Cited

U.S. PATENT DOCUMENTS

| | | |
|---|---|---|
| 7,651,596 B2 | 1/2010 | Petisce et al. |
| 7,651,845 B2 | 1/2010 | Doyle, III et al. |
| 7,653,425 B2 | 1/2010 | Hayter et al. |
| 7,654,956 B2 | 2/2010 | Brister et al. |
| 7,657,297 B2 | 2/2010 | Simpson et al. |
| 7,659,823 B1 | 2/2010 | Killian et al. |
| 7,699,775 B2 | 4/2010 | Desai et al. |
| 7,699,964 B2 | 4/2010 | Feldman et al. |
| 7,711,402 B2 | 5/2010 | Shults et al. |
| 7,713,574 B2 | 5/2010 | Brister et al. |
| 7,715,893 B2 | 5/2010 | Kamath et al. |
| 7,741,734 B2 | 6/2010 | Joannopoulos et al. |
| 7,766,829 B2 | 8/2010 | Sloan et al. |
| 7,768,386 B2 | 8/2010 | Hayter et al. |
| 7,768,387 B2 | 8/2010 | Fennell et al. |
| 7,775,444 B2 | 8/2010 | DeRocco et al. |
| 7,778,680 B2 | 8/2010 | Goode et al. |
| 7,779,332 B2 | 8/2010 | Karr et al. |
| 7,811,231 B2 | 10/2010 | Jin et al. |
| 7,813,809 B2 | 10/2010 | Strother et al. |
| 7,826,382 B2 | 11/2010 | Sicurello et al. |
| 7,826,981 B2 | 11/2010 | Goode, Jr. et al. |
| 7,889,069 B2 | 2/2011 | Fifolt et al. |
| 7,899,545 B2 | 3/2011 | John |
| 7,905,833 B2 | 3/2011 | Brister et al. |
| 7,914,450 B2 | 3/2011 | Goode, Jr. et al. |
| 7,920,906 B2 | 4/2011 | Goode et al. |
| 7,928,850 B2 | 4/2011 | Hayter et al. |
| 7,941,200 B2 | 5/2011 | Weinert et al. |
| 7,946,985 B2 | 5/2011 | Mastrototaro et al. |
| 7,972,296 B2 | 7/2011 | Braig et al. |
| 7,976,466 B2 | 7/2011 | Ward et al. |
| 7,978,063 B2 | 7/2011 | Baldus et al. |
| 8,010,174 B2 | 8/2011 | Goode et al. |
| 8,192,394 B2 | 6/2012 | Estes et al. |
| 8,216,138 B1 | 7/2012 | McGarraugh et al. |
| 8,282,549 B2 | 10/2012 | Brauker et al. |
| 8,478,557 B2 * | 7/2013 | Hayter et al. ................ 702/104 |
| 2001/0037366 A1 | 11/2001 | Webb et al. |
| 2002/0019022 A1 | 2/2002 | Dunn et al. |
| 2002/0019612 A1 | 2/2002 | Watanabe et al. |
| 2002/0042090 A1 | 4/2002 | Heller et al. |
| 2002/0054320 A1 | 5/2002 | Ogino |
| 2002/0068860 A1 | 6/2002 | Clark |
| 2002/0095076 A1 | 7/2002 | Krausman et al. |
| 2002/0103499 A1 | 8/2002 | Perez et al. |
| 2002/0106709 A1 | 8/2002 | Potts et al. |
| 2002/0128594 A1 | 9/2002 | Das et al. |
| 2002/0147135 A1 | 10/2002 | Schnell |
| 2002/0161288 A1 | 10/2002 | Shin et al. |
| 2002/0169439 A1 | 11/2002 | Flaherty et al. |
| 2002/0169635 A1 | 11/2002 | Shillingburg |
| 2003/0004403 A1 | 1/2003 | Drinan et al. |
| 2003/0023317 A1 | 1/2003 | Brauker et al. |
| 2003/0028089 A1 | 2/2003 | Galley et al. |
| 2003/0032874 A1 | 2/2003 | Rhodes et al. |
| 2003/0042137 A1 | 3/2003 | Mao et al. |
| 2003/0055380 A1 | 3/2003 | Flaherty et al. |
| 2003/0060692 A1 | 3/2003 | Ruchti et al. |
| 2003/0060753 A1 | 3/2003 | Starkweather et al. |
| 2003/0065308 A1 | 4/2003 | Lebel et al. |
| 2003/0100040 A1 | 5/2003 | Bonnecaze et al. |
| 2003/0100821 A1 | 5/2003 | Heller et al. |
| 2003/0114897 A1 | 6/2003 | Von Arx et al. |
| 2003/0125612 A1 | 7/2003 | Fox et al. |
| 2003/0130616 A1 | 7/2003 | Steil et al. |
| 2003/0134347 A1 | 7/2003 | Heller et al. |
| 2003/0147515 A1 | 8/2003 | Kai et al. |
| 2003/0167035 A1 | 9/2003 | Flaherty et al. |
| 2003/0168338 A1 | 9/2003 | Gao et al. |
| 2003/0176933 A1 | 9/2003 | Lebel et al. |
| 2003/0187338 A1 | 10/2003 | Say et al. |
| 2003/0191377 A1 | 10/2003 | Robinson et al. |
| 2003/0199790 A1 | 10/2003 | Boecker et al. |
| 2003/0208113 A1 | 11/2003 | Mault et al. |
| 2003/0212317 A1 | 11/2003 | Kovatchev et al. |
| 2003/0212379 A1 | 11/2003 | Bylund et al. |
| 2003/0216630 A1 | 11/2003 | Jersey-Willuhn et al. |
| 2003/0217966 A1 | 11/2003 | Tapsak et al. |
| 2003/0225361 A1 | 12/2003 | Sabra |
| 2004/0010186 A1 | 1/2004 | Kimball et al. |
| 2004/0010207 A1 | 1/2004 | Flaherty et al. |
| 2004/0011671 A1 | 1/2004 | Shults et al. |
| 2004/0015131 A1 | 1/2004 | Flaherty et al. |
| 2004/0024553 A1 | 2/2004 | Monfre et al. |
| 2004/0034289 A1 | 2/2004 | Teller et al. |
| 2004/0039298 A1 | 2/2004 | Abreu |
| 2004/0040840 A1 | 3/2004 | Mao et al. |
| 2004/0041749 A1 | 3/2004 | Dixon |
| 2004/0045879 A1 | 3/2004 | Shults et al. |
| 2004/0063435 A1 | 4/2004 | Sakamoto et al. |
| 2004/0064068 A1 | 4/2004 | DeNuzzio et al. |
| 2004/0064088 A1 | 4/2004 | Gorman et al. |
| 2004/0064096 A1 | 4/2004 | Flaherty et al. |
| 2004/0099529 A1 | 5/2004 | Mao et al. |
| 2004/0106858 A1 | 6/2004 | Say et al. |
| 2004/0122353 A1 | 6/2004 | Shahmirian et al. |
| 2004/0133164 A1 | 7/2004 | Funderburk et al. |
| 2004/0133390 A1 | 7/2004 | Osorio et al. |
| 2004/0138588 A1 | 7/2004 | Saikley et al. |
| 2004/0146909 A1 | 7/2004 | Duong et al. |
| 2004/0147872 A1 | 7/2004 | Thompson |
| 2004/0152622 A1 | 8/2004 | Keith et al. |
| 2004/0153032 A1 | 8/2004 | Garribotto et al. |
| 2004/0167464 A1 | 8/2004 | Ireland et al. |
| 2004/0167801 A1 | 8/2004 | Say et al. |
| 2004/0171921 A1 | 9/2004 | Say et al. |
| 2004/0176672 A1 | 9/2004 | Silver et al. |
| 2004/0186362 A1 | 9/2004 | Brauker et al. |
| 2004/0186365 A1 | 9/2004 | Jin et al. |
| 2004/0193025 A1 | 9/2004 | Steil et al. |
| 2004/0193090 A1 | 9/2004 | Lebel et al. |
| 2004/0197846 A1 | 10/2004 | Hockersmith et al. |
| 2004/0199059 A1 | 10/2004 | Brauker et al. |
| 2004/0204687 A1 | 10/2004 | Mogensen et al. |
| 2004/0204868 A1 | 10/2004 | Maynard et al. |
| 2004/0219664 A1 | 11/2004 | Heller et al. |
| 2004/0225338 A1 | 11/2004 | Lebel et al. |
| 2004/0236200 A1 | 11/2004 | Say et al. |
| 2004/0254433 A1 | 12/2004 | Bandis et al. |
| 2004/0260478 A1 | 12/2004 | Schwamm |
| 2004/0267300 A1 | 12/2004 | Mace |
| 2005/0001024 A1 | 1/2005 | Kusaka et al. |
| 2005/0004439 A1 | 1/2005 | Shin et al. |
| 2005/0004494 A1 | 1/2005 | Perez et al. |
| 2005/0010269 A1 | 1/2005 | Lebel et al. |
| 2005/0027177 A1 | 2/2005 | Shin et al. |
| 2005/0027180 A1 | 2/2005 | Goode et al. |
| 2005/0027181 A1 | 2/2005 | Goode et al. |
| 2005/0027462 A1 | 2/2005 | Goode et al. |
| 2005/0027463 A1 | 2/2005 | Goode et al. |
| 2005/0031689 A1 | 2/2005 | Shults et al. |
| 2005/0038332 A1 | 2/2005 | Saidara et al. |
| 2005/0043598 A1 | 2/2005 | Goode, Jr. et al. |
| 2005/0049179 A1 | 3/2005 | Davidson et al. |
| 2005/0070777 A1 | 3/2005 | Cho et al. |
| 2005/0090607 A1 | 4/2005 | Tapsak et al. |
| 2005/0096511 A1 | 5/2005 | Fox et al. |
| 2005/0096512 A1 | 5/2005 | Fox et al. |
| 2005/0096516 A1 | 5/2005 | Soykan et al. |
| 2005/0112169 A1 | 5/2005 | Brauker et al. |
| 2005/0113653 A1 | 5/2005 | Fox et al. |
| 2005/0113886 A1 | 5/2005 | Fischell et al. |
| 2005/0114068 A1 | 5/2005 | Chey et al. |
| 2005/0116683 A1 | 6/2005 | Cheng et al. |
| 2005/0121322 A1 | 6/2005 | Say et al. |
| 2005/0131346 A1 | 6/2005 | Douglas |
| 2005/0137530 A1 | 6/2005 | Campbell et al. |
| 2005/0143635 A1 | 6/2005 | Kamath et al. |
| 2005/0176136 A1 | 8/2005 | Burd et al. |
| 2005/0177398 A1 | 8/2005 | Watanabe et al. |
| 2005/0182306 A1 | 8/2005 | Sloan |
| 2005/0187442 A1 | 8/2005 | Cho et al. |
| 2005/0187720 A1 | 8/2005 | Goode, Jr. et al. |

(56) References Cited

U.S. PATENT DOCUMENTS

| | | |
|---|---|---|
| 2005/0192494 A1 | 9/2005 | Ginsberg |
| 2005/0192557 A1 | 9/2005 | Brauker et al. |
| 2005/0195930 A1 | 9/2005 | Spital et al. |
| 2005/0199494 A1 | 9/2005 | Say et al. |
| 2005/0203360 A1 | 9/2005 | Brauker et al. |
| 2005/0204134 A1 | 9/2005 | Von Arx et al. |
| 2005/0214892 A1 | 9/2005 | Kovatchev et al. |
| 2005/0236361 A1 | 10/2005 | Ufer et al. |
| 2005/0239154 A1 | 10/2005 | Feldman et al. |
| 2005/0241957 A1 | 11/2005 | Mao et al. |
| 2005/0245795 A1 | 11/2005 | Goode, Jr. et al. |
| 2005/0245799 A1 | 11/2005 | Brauker et al. |
| 2005/0245839 A1 | 11/2005 | Stivoric et al. |
| 2005/0245904 A1 | 11/2005 | Estes et al. |
| 2005/0251033 A1 | 11/2005 | Scarantino et al. |
| 2005/0272985 A1 | 12/2005 | Kotulla et al. |
| 2005/0277912 A1 | 12/2005 | John |
| 2005/0287620 A1 | 12/2005 | Heller et al. |
| 2006/0001538 A1 | 1/2006 | Kraft et al. |
| 2006/0001551 A1 | 1/2006 | Kraft et al. |
| 2006/0004270 A1 | 1/2006 | Bedard et al. |
| 2006/0015020 A1 | 1/2006 | Neale et al. |
| 2006/0015024 A1 | 1/2006 | Brister et al. |
| 2006/0016700 A1 | 1/2006 | Brister et al. |
| 2006/0017923 A1 | 1/2006 | Ruchti et al. |
| 2006/0019327 A1 | 1/2006 | Brister et al. |
| 2006/0020186 A1 | 1/2006 | Brister et al. |
| 2006/0020187 A1 | 1/2006 | Brister et al. |
| 2006/0020188 A1 | 1/2006 | Kamath et al. |
| 2006/0020189 A1 | 1/2006 | Brister et al. |
| 2006/0020190 A1 | 1/2006 | Kamath et al. |
| 2006/0020191 A1 | 1/2006 | Brister et al. |
| 2006/0020192 A1 | 1/2006 | Brister et al. |
| 2006/0020300 A1 | 1/2006 | Nghiem et al. |
| 2006/0025663 A1 | 2/2006 | Talbot et al. |
| 2006/0029177 A1 | 2/2006 | Cranford, Jr. et al. |
| 2006/0031094 A1 | 2/2006 | Cohen et al. |
| 2006/0036139 A1 | 2/2006 | Brister et al. |
| 2006/0036140 A1 | 2/2006 | Brister et al. |
| 2006/0036141 A1 | 2/2006 | Kamath et al. |
| 2006/0036142 A1 | 2/2006 | Brister et al. |
| 2006/0036143 A1 | 2/2006 | Brister et al. |
| 2006/0036144 A1 | 2/2006 | Brister et al. |
| 2006/0036145 A1 | 2/2006 | Brister et al. |
| 2006/0091006 A1 | 5/2006 | Wang et al. |
| 2006/0142651 A1 | 6/2006 | Brister et al. |
| 2006/0154642 A1 | 7/2006 | Scannell |
| 2006/0155180 A1 | 7/2006 | Brister et al. |
| 2006/0156796 A1 | 7/2006 | Burke et al. |
| 2006/0166629 A1 | 7/2006 | Reggiardo |
| 2006/0173260 A1 | 8/2006 | Gaoni et al. |
| 2006/0173406 A1 | 8/2006 | Hayes et al. |
| 2006/0173444 A1 | 8/2006 | Choy et al. |
| 2006/0183985 A1 | 8/2006 | Brister et al. |
| 2006/0189863 A1 | 8/2006 | Peyser et al. |
| 2006/0202805 A1 | 9/2006 | Schulman et al. |
| 2006/0211072 A1 | 9/2006 | Ryan et al. |
| 2006/0222566 A1 | 10/2006 | Brauker et al. |
| 2006/0224109 A1 | 10/2006 | Steil et al. |
| 2006/0224141 A1 | 10/2006 | Rush et al. |
| 2006/0229512 A1 | 10/2006 | Petisce et al. |
| 2006/0247508 A1 | 11/2006 | Fennell |
| 2006/0253296 A1 | 11/2006 | Liisberg et al. |
| 2006/0258929 A1 | 11/2006 | Goode et al. |
| 2006/0272652 A1 | 12/2006 | Stocker et al. |
| 2006/0281985 A1 | 12/2006 | Ward et al. |
| 2006/0290496 A1 | 12/2006 | Peeters et al. |
| 2006/0293607 A1 | 12/2006 | Alt et al. |
| 2007/0007133 A1 | 1/2007 | Mang et al. |
| 2007/0010950 A1 | 1/2007 | Abensour et al. |
| 2007/0016381 A1 | 1/2007 | Kamath et al. |
| 2007/0017983 A1 | 1/2007 | Frank et al. |
| 2007/0027381 A1 | 2/2007 | Stafford |
| 2007/0032706 A1 | 2/2007 | Kamath et al. |
| 2007/0032717 A1 | 2/2007 | Brister et al. |
| 2007/0033074 A1 | 2/2007 | Nitzan et al. |
| 2007/0060803 A1 | 3/2007 | Liljeryd et al. |
| 2007/0060814 A1 | 3/2007 | Stafford |
| 2007/0060869 A1 | 3/2007 | Tolle et al. |
| 2007/0060979 A1 | 3/2007 | Strother et al. |
| 2007/0066873 A1 | 3/2007 | Kamath et al. |
| 2007/0066956 A1 | 3/2007 | Finkel |
| 2007/0071681 A1 | 3/2007 | Gadkar et al. |
| 2007/0073129 A1 | 3/2007 | Shah et al. |
| 2007/0078320 A1 | 4/2007 | Stafford |
| 2007/0078321 A1 | 4/2007 | Mazza et al. |
| 2007/0078322 A1 | 4/2007 | Stafford |
| 2007/0078323 A1 | 4/2007 | Reggiardo et al. |
| 2007/0078818 A1 | 4/2007 | Zivitz et al. |
| 2007/0093786 A1 | 4/2007 | Goldsmith et al. |
| 2007/0094216 A1 | 4/2007 | Mathias et al. |
| 2007/0100222 A1 | 5/2007 | Mastrototaro et al. |
| 2007/0106135 A1 | 5/2007 | Sloan et al. |
| 2007/0118405 A1 | 5/2007 | Campbell et al. |
| 2007/0124002 A1 | 5/2007 | Estes et al. |
| 2007/0149875 A1 | 6/2007 | Ouyang et al. |
| 2007/0153705 A1 | 7/2007 | Rosar et al. |
| 2007/0156094 A1 | 7/2007 | Safabash et al. |
| 2007/0163880 A1 | 7/2007 | Woo et al. |
| 2007/0168224 A1 | 7/2007 | Letzt et al. |
| 2007/0173706 A1 | 7/2007 | Neinast et al. |
| 2007/0173761 A1 | 7/2007 | Kanderian et al. |
| 2007/0179349 A1 | 8/2007 | Hoyme et al. |
| 2007/0179352 A1 | 8/2007 | Randlov et al. |
| 2007/0191701 A1 | 8/2007 | Feldman et al. |
| 2007/0191702 A1 | 8/2007 | Yodfat et al. |
| 2007/0203407 A1 | 8/2007 | Hoss et al. |
| 2007/0203966 A1 | 8/2007 | Brauker et al. |
| 2007/0208246 A1 | 9/2007 | Brauker et al. |
| 2007/0213657 A1 | 9/2007 | Jennewine et al. |
| 2007/0228071 A1 | 10/2007 | Kamen et al. |
| 2007/0235331 A1 | 10/2007 | Simpson et al. |
| 2007/0249922 A1 | 10/2007 | Peyser et al. |
| 2007/0255348 A1 | 11/2007 | Holtzclaw |
| 2007/0271285 A1 | 11/2007 | Eichorn et al. |
| 2007/0282299 A1 | 12/2007 | Hellwig |
| 2007/0299617 A1 | 12/2007 | Willis |
| 2008/0009692 A1 | 1/2008 | Stafford |
| 2008/0017522 A1 | 1/2008 | Heller et al. |
| 2008/0021436 A1 | 1/2008 | Wolpert et al. |
| 2008/0021666 A1 | 1/2008 | Goode, Jr. et al. |
| 2008/0029391 A1 | 2/2008 | Mao et al. |
| 2008/0033254 A1 | 2/2008 | Kamath et al. |
| 2008/0039702 A1 | 2/2008 | Hayter et al. |
| 2008/0045824 A1 | 2/2008 | Tapsak et al. |
| 2008/0057484 A1 | 3/2008 | Miyata et al. |
| 2008/0058625 A1 | 3/2008 | McGarraugh et al. |
| 2008/0058626 A1 | 3/2008 | Miyata et al. |
| 2008/0058678 A1 | 3/2008 | Miyata et al. |
| 2008/0058773 A1 | 3/2008 | John |
| 2008/0060955 A1 | 3/2008 | Goodnow |
| 2008/0061961 A1 | 3/2008 | John |
| 2008/0064937 A1 | 3/2008 | McGarraugh et al. |
| 2008/0071156 A1 | 3/2008 | Brister et al. |
| 2008/0071157 A1 | 3/2008 | McGarraugh et al. |
| 2008/0071158 A1 | 3/2008 | McGarraugh et al. |
| 2008/0081977 A1 | 4/2008 | Hayter et al. |
| 2008/0083617 A1 | 4/2008 | Simpson et al. |
| 2008/0086042 A1 | 4/2008 | Brister et al. |
| 2008/0086044 A1 | 4/2008 | Brister et al. |
| 2008/0086273 A1 | 4/2008 | Shults et al. |
| 2008/0092638 A1 | 4/2008 | Brenneman et al. |
| 2008/0097289 A1 | 4/2008 | Steil et al. |
| 2008/0108942 A1 | 5/2008 | Brister et al. |
| 2008/0139910 A1 | 6/2008 | Mastrototaro et al. |
| 2008/0154513 A1 | 6/2008 | Kovatchev et al. |
| 2008/0161666 A1 | 7/2008 | Feldman et al. |
| 2008/0167543 A1 | 7/2008 | Say et al. |
| 2008/0172205 A1 | 7/2008 | Breton et al. |
| 2008/0177149 A1 | 7/2008 | Weinert et al. |
| 2008/0182537 A1 | 7/2008 | Manku et al. |
| 2008/0183060 A1 | 7/2008 | Steil et al. |
| 2008/0183061 A1 | 7/2008 | Goode et al. |
| 2008/0183399 A1 | 7/2008 | Goode et al. |

(56) References Cited

U.S. PATENT DOCUMENTS

| | | |
|---|---|---|
| 2008/0188731 A1 | 8/2008 | Brister et al. |
| 2008/0188796 A1 | 8/2008 | Steil et al. |
| 2008/0189051 A1 | 8/2008 | Goode et al. |
| 2008/0194934 A1 | 8/2008 | Ray et al. |
| 2008/0194935 A1 | 8/2008 | Brister et al. |
| 2008/0194936 A1 | 8/2008 | Goode et al. |
| 2008/0194937 A1 | 8/2008 | Goode et al. |
| 2008/0194938 A1 | 8/2008 | Brister et al. |
| 2008/0195232 A1 | 8/2008 | Carr-Brendel et al. |
| 2008/0195967 A1 | 8/2008 | Goode et al. |
| 2008/0197024 A1 | 8/2008 | Simpson et al. |
| 2008/0200788 A1 | 8/2008 | Brister et al. |
| 2008/0200789 A1 | 8/2008 | Brister et al. |
| 2008/0200791 A1 | 8/2008 | Simpson et al. |
| 2008/0208025 A1 | 8/2008 | Shults et al. |
| 2008/0208026 A1 | 8/2008 | Noujaim et al. |
| 2008/0208113 A1 | 8/2008 | Damiano et al. |
| 2008/0214900 A1 | 9/2008 | Fennell et al. |
| 2008/0214915 A1 | 9/2008 | Brister et al. |
| 2008/0214918 A1 | 9/2008 | Brister et al. |
| 2008/0228051 A1 | 9/2008 | Shults et al. |
| 2008/0228054 A1 | 9/2008 | Shults et al. |
| 2008/0228055 A1 | 9/2008 | Sher |
| 2008/0234663 A1 | 9/2008 | Yodfat et al. |
| 2008/0242961 A1 | 10/2008 | Brister et al. |
| 2008/0242963 A1 | 10/2008 | Essenpreis et al. |
| 2008/0255434 A1 | 10/2008 | Hayter et al. |
| 2008/0255437 A1 | 10/2008 | Hayter |
| 2008/0255808 A1 | 10/2008 | Hayter |
| 2008/0256048 A1 | 10/2008 | Hayter |
| 2008/0262469 A1 | 10/2008 | Brister et al. |
| 2008/0269723 A1 | 10/2008 | Mastrototaro et al. |
| 2008/0275313 A1 | 11/2008 | Brister et al. |
| 2008/0287761 A1 | 11/2008 | Hayter |
| 2008/0287762 A1 | 11/2008 | Hayter |
| 2008/0287763 A1 | 11/2008 | Hayter |
| 2008/0287764 A1 | 11/2008 | Rasdal et al. |
| 2008/0287765 A1 | 11/2008 | Rasdal et al. |
| 2008/0287766 A1 | 11/2008 | Rasdal et al. |
| 2008/0288180 A1 | 11/2008 | Hayter |
| 2008/0288204 A1 | 11/2008 | Hayter et al. |
| 2008/0296155 A1 | 12/2008 | Shults et al. |
| 2008/0300572 A1 | 12/2008 | Rankers et al. |
| 2008/0306368 A1 | 12/2008 | Goode, et al. |
| 2008/0306434 A1 | 12/2008 | Dobbles et al. |
| 2008/0306435 A1 | 12/2008 | Kamath et al. |
| 2008/0306444 A1 | 12/2008 | Brister et al. |
| 2008/0312841 A1 | 12/2008 | Hayter |
| 2008/0312842 A1 | 12/2008 | Hayter |
| 2008/0312844 A1 | 12/2008 | Hayter et al. |
| 2008/0312845 A1 | 12/2008 | Hayter et al. |
| 2008/0314395 A1 | 12/2008 | Kovatchev et al. |
| 2008/0319085 A1 | 12/2008 | Wright et al. |
| 2008/0319279 A1 | 12/2008 | Ramsay et al. |
| 2008/0319295 A1 | 12/2008 | Bernstein et al. |
| 2008/0319296 A1 | 12/2008 | Bernstein et al. |
| 2009/0005665 A1 | 1/2009 | Hayter et al. |
| 2009/0005666 A1 | 1/2009 | Shin et al. |
| 2009/0006034 A1 | 1/2009 | Hayter et al. |
| 2009/0006133 A1 | 1/2009 | Weinert et al. |
| 2009/0012379 A1 | 1/2009 | Goode et al. |
| 2009/0018424 A1 | 1/2009 | Kamath et al. |
| 2009/0018425 A1 | 1/2009 | Ouyang et al. |
| 2009/0030294 A1 | 1/2009 | Petisce et al. |
| 2009/0033482 A1 | 2/2009 | Hayter et al. |
| 2009/0036747 A1 | 2/2009 | Hayter et al. |
| 2009/0036758 A1 | 2/2009 | Brauker et al. |
| 2009/0036760 A1 | 2/2009 | Hayter |
| 2009/0036763 A1 | 2/2009 | Brauker et al. |
| 2009/0040022 A1 | 2/2009 | Finkenzeller |
| 2009/0043181 A1 | 2/2009 | Brauker et al. |
| 2009/0043182 A1 | 2/2009 | Brauker et al. |
| 2009/0043525 A1 | 2/2009 | Brauker et al. |
| 2009/0043541 A1 | 2/2009 | Brauker et al. |
| 2009/0043542 A1 | 2/2009 | Brauker et al. |
| 2009/0045055 A1 | 2/2009 | Rhodes et al. |
| 2009/0048503 A1 | 2/2009 | Dalal et al. |
| 2009/0054747 A1 | 2/2009 | Fennell |
| 2009/0054748 A1 | 2/2009 | Feldman et al. |
| 2009/0055149 A1 | 2/2009 | Hayter et al. |
| 2009/0062633 A1 | 3/2009 | Brauker et al. |
| 2009/0062635 A1 | 3/2009 | Brauker et al. |
| 2009/0062767 A1 | 3/2009 | VanAntwerp et al. |
| 2009/0063402 A1 | 3/2009 | Hayter |
| 2009/0076356 A1 | 3/2009 | Simpson et al. |
| 2009/0076360 A1 | 3/2009 | Brister et al. |
| 2009/0076361 A1 | 3/2009 | Kamath et al. |
| 2009/0082693 A1 | 3/2009 | Stafford |
| 2009/0085873 A1 | 4/2009 | Betts et al. |
| 2009/0088614 A1 | 4/2009 | Taub et al. |
| 2009/0099436 A1 | 4/2009 | Brister et al. |
| 2009/0105560 A1 | 4/2009 | Solomon |
| 2009/0105570 A1 | 4/2009 | Sloan et al. |
| 2009/0105571 A1 | 4/2009 | Fennell et al. |
| 2009/0105636 A1 | 4/2009 | Hayter et al. |
| 2009/0124877 A1 | 5/2009 | Goode et al. |
| 2009/0124878 A1 | 5/2009 | Goode et al. |
| 2009/0124879 A1 | 5/2009 | Brister et al. |
| 2009/0124964 A1 | 5/2009 | Leach et al. |
| 2009/0131768 A1 | 5/2009 | Simpson et al. |
| 2009/0131769 A1 | 5/2009 | Leach et al. |
| 2009/0131776 A1 | 5/2009 | Simpson et al. |
| 2009/0131777 A1 | 5/2009 | Simpson et al. |
| 2009/0137886 A1 | 5/2009 | Shariati et al. |
| 2009/0137887 A1 | 5/2009 | Shariati et al. |
| 2009/0143659 A1 | 6/2009 | Li et al. |
| 2009/0143660 A1 | 6/2009 | Brister et al. |
| 2009/0156919 A1 | 6/2009 | Brister et al. |
| 2009/0156924 A1 | 6/2009 | Shariati et al. |
| 2009/0163790 A1 | 6/2009 | Brister et al. |
| 2009/0163791 A1 | 6/2009 | Brister et al. |
| 2009/0164190 A1 | 6/2009 | Hayter |
| 2009/0164239 A1 | 6/2009 | Hayter et al. |
| 2009/0164251 A1 | 6/2009 | Hayter |
| 2009/0178459 A1 | 7/2009 | Li et al. |
| 2009/0182217 A1 | 7/2009 | Li et al. |
| 2009/0192366 A1 | 7/2009 | Mensinger et al. |
| 2009/0192380 A1 | 7/2009 | Shariati et al. |
| 2009/0192722 A1 | 7/2009 | Shariati et al. |
| 2009/0192724 A1 | 7/2009 | Brauker et al. |
| 2009/0192745 A1 | 7/2009 | Kamath et al. |
| 2009/0192751 A1 | 7/2009 | Kamath et al. |
| 2009/0198118 A1 | 8/2009 | Hayter et al. |
| 2009/0203981 A1 | 8/2009 | Brauker et al. |
| 2009/0204341 A1 | 8/2009 | Brauker et al. |
| 2009/0216100 A1 | 8/2009 | Ebner et al. |
| 2009/0216103 A1 | 8/2009 | Brister et al. |
| 2009/0227855 A1 | 9/2009 | Hill et al. |
| 2009/0240120 A1 | 9/2009 | Mensinger et al. |
| 2009/0240128 A1 | 9/2009 | Mensinger et al. |
| 2009/0240193 A1 | 9/2009 | Mensinger et al. |
| 2009/0240440 A1 | 9/2009 | Shurabura et al. |
| 2009/0242399 A1 | 10/2009 | Kamath et al. |
| 2009/0242425 A1 | 10/2009 | Kamath et al. |
| 2009/0247855 A1 | 10/2009 | Boock et al. |
| 2009/0247856 A1 | 10/2009 | Boock et al. |
| 2009/0247857 A1 | 10/2009 | Harper et al. |
| 2009/0247931 A1 | 10/2009 | Damgaard-Sorensen |
| 2009/0253973 A1 | 10/2009 | Bashan et al. |
| 2009/0259118 A1 | 10/2009 | Feldman et al. |
| 2009/0287073 A1 | 11/2009 | Boock et al. |
| 2009/0287074 A1 | 11/2009 | Shults et al. |
| 2009/0292188 A1 | 11/2009 | Hoss et al. |
| 2009/0296742 A1 | 12/2009 | Sicurello et al. |
| 2009/0298182 A1 | 12/2009 | Schulat et al. |
| 2009/0299155 A1 | 12/2009 | Yang et al. |
| 2009/0299156 A1 | 12/2009 | Simpson et al. |
| 2009/0299162 A1 | 12/2009 | Brauker et al. |
| 2009/0299276 A1 | 12/2009 | Brauker et al. |
| 2010/0010324 A1 | 1/2010 | Brauker et al. |
| 2010/0010329 A1 | 1/2010 | Taub et al. |
| 2010/0010331 A1 | 1/2010 | Brauker et al. |
| 2010/0010332 A1 | 1/2010 | Brauker et al. |
| 2010/0016687 A1 | 1/2010 | Brauker et al. |

(56) References Cited

U.S. PATENT DOCUMENTS

| | | | |
|---|---|---|---|
| 2010/0016698 A1 | 1/2010 | Rasdal et al. |
| 2010/0022855 A1 | 1/2010 | Brauker et al. |
| 2010/0030038 A1 | 2/2010 | Brauker et al. |
| 2010/0030053 A1 | 2/2010 | Goode, Jr. et al. |
| 2010/0030484 A1 | 2/2010 | Brauker et al. |
| 2010/0030485 A1 | 2/2010 | Brauker et al. |
| 2010/0036215 A1 | 2/2010 | Goode, Jr. et al. |
| 2010/0036216 A1 | 2/2010 | Goode, Jr. et al. |
| 2010/0036222 A1 | 2/2010 | Goode, Jr. et al. |
| 2010/0036223 A1 | 2/2010 | Goode, Jr. et al. |
| 2010/0036225 A1 | 2/2010 | Goode, Jr. et al. |
| 2010/0041971 A1 | 2/2010 | Goode, Jr. et al. |
| 2010/0045465 A1 | 2/2010 | Brauker et al. |
| 2010/0049024 A1 | 2/2010 | Saint et al. |
| 2010/0056992 A1 | 3/2010 | Hayter et al. |
| 2010/0057040 A1 | 3/2010 | Hayter |
| 2010/0057041 A1 | 3/2010 | Hayter |
| 2010/0057042 A1 | 3/2010 | Hayter |
| 2010/0057044 A1 | 3/2010 | Hayter |
| 2010/0057057 A1 | 3/2010 | Hayter et al. |
| 2010/0063373 A1 | 3/2010 | Kamath et al. |
| 2010/0076283 A1 | 3/2010 | Simpson et al. |
| 2010/0081906 A1 | 4/2010 | Hayter et al. |
| 2010/0081908 A1 | 4/2010 | Dobbles et al. |
| 2010/0081909 A1 | 4/2010 | Budiman et al. |
| 2010/0081910 A1 | 4/2010 | Brister et al. |
| 2010/0087724 A1 | 4/2010 | Brauker et al. |
| 2010/0096259 A1 | 4/2010 | Zhang et al. |
| 2010/0099970 A1 | 4/2010 | Shults et al. |
| 2010/0099971 A1 | 4/2010 | Shults et al. |
| 2010/0105999 A1 | 4/2010 | Dixon et al. |
| 2010/0119693 A1 | 5/2010 | Tapsak et al. |
| 2010/0121169 A1 | 5/2010 | Petisce et al. |
| 2010/0141656 A1 | 6/2010 | Krieftewirth |
| 2010/0152554 A1 | 6/2010 | Steine et al. |
| 2010/0160759 A1 | 6/2010 | Celentano et al. |
| 2010/0168538 A1 | 7/2010 | Keenan et al. |
| 2010/0168546 A1 | 7/2010 | Kamath et al. |
| 2010/0191082 A1 | 7/2010 | Brister et al. |
| 2010/0191085 A1 | 7/2010 | Budiman |
| 2010/0191472 A1 | 7/2010 | Doniger et al. |
| 2010/0198034 A1 | 8/2010 | Thomas et al. |
| 2010/0198142 A1 | 8/2010 | Sloan et al. |
| 2010/0213080 A1 | 8/2010 | Celentano et al. |
| 2010/0234710 A1 | 9/2010 | Budiman et al. |
| 2010/0240975 A1 | 9/2010 | Goode et al. |
| 2010/0274111 A1 | 10/2010 | Say et al. |
| 2010/0274515 A1 | 10/2010 | Hoss et al. |
| 2010/0275108 A1 | 10/2010 | Sloan et al. |
| 2010/0312176 A1 | 12/2010 | Lauer et al. |
| 2011/0024043 A1 | 2/2011 | Boock et al. |
| 2011/0024307 A1 | 2/2011 | Simpson et al. |
| 2011/0027127 A1 | 2/2011 | Simpson et al. |
| 2011/0027453 A1 | 2/2011 | Boock et al. |
| 2011/0027458 A1 | 2/2011 | Boock et al. |
| 2011/0028815 A1 | 2/2011 | Simpson et al. |
| 2011/0028816 A1 | 2/2011 | Simpson et al. |
| 2011/0054282 A1 | 3/2011 | Nekoomaram et al. |
| 2011/0060530 A1 | 3/2011 | Fennell |
| 2011/0077490 A1 | 3/2011 | Simpson et al. |
| 2011/0148905 A1 | 6/2011 | Simmons et al. |
| 2011/0208027 A1 | 8/2011 | Wagner et al. |
| 2011/0257895 A1 | 10/2011 | Brauker et al. |
| 2011/0320130 A1 | 12/2011 | Valdes et al. |
| 2012/0078071 A1 | 3/2012 | Bohm et al. |
| 2012/0088995 A1 | 4/2012 | Fennell et al. |
| 2012/0108934 A1 | 5/2012 | Valdes et al. |
| 2012/0173200 A1 | 7/2012 | Breton et al. |
| 2012/0190989 A1 | 7/2012 | Kaiser et al. |

FOREIGN PATENT DOCUMENTS

| | | |
|---|---|---|
| CA | 2498682 | 9/2005 |
| CA | 2555749 | 9/2005 |
| CA | 2632709 | 6/2007 |
| CA | 2615575 | 6/2008 |
| CA | 2701374 | 4/2009 |
| DE | 4401400 | 7/1995 |
| EP | 0098592 | 1/1984 |
| EP | 0127958 | 12/1984 |
| EP | 0320109 | 6/1989 |
| EP | 0353328 | 2/1990 |
| EP | 0390390 | 10/1990 |
| EP | 0396788 | 11/1990 |
| EP | 0286118 | 1/1995 |
| EP | 1048264 | 11/2000 |
| EP | 1568309 | 8/2005 |
| EP | 1956371 | 8/2008 |
| EP | 2260757 | 12/2010 |
| WO | WO-93/06237 | 4/1993 |
| WO | WO-96/25089 | 8/1996 |
| WO | WO-96/35370 | 11/1996 |
| WO | WO-98/35053 | 8/1998 |
| WO | WO-99/56613 | 11/1999 |
| WO | WO-00/49940 | 8/2000 |
| WO | WO-00/59370 | 10/2000 |
| WO | WO-00/74753 | 12/2000 |
| WO | WO-00/78992 | 12/2000 |
| WO | WO-01/52935 | 7/2001 |
| WO | WO-01/54753 | 8/2001 |
| WO | WO-02/16905 | 2/2002 |
| WO | WO-02/058537 | 8/2002 |
| WO | WO-03/076893 | 9/2003 |
| WO | WO-03/082091 | 10/2003 |
| WO | WO-03/085372 | 10/2003 |
| WO | WO-2004/015539 | 2/2004 |
| WO | WO-2004/047445 | 6/2004 |
| WO | WO-2004/061420 | 7/2004 |
| WO | WO-2005/040404 | 5/2005 |
| WO | WO-2005/041766 | 5/2005 |
| WO | WO-2005/089103 | 9/2005 |
| WO | WO-2006/024671 | 3/2006 |
| WO | WO-2006/051466 | 5/2006 |
| WO | WO-2006/064397 | 6/2006 |
| WO | WO-2006/079114 | 7/2006 |
| WO | WO-2006/118947 | 11/2006 |
| WO | WO-2007/007459 | 1/2007 |
| WO | WO-2007/016399 | 2/2007 |
| WO | WO-2007/027788 | 3/2007 |
| WO | WO-2007/041069 | 4/2007 |
| WO | WO-2007/041070 | 4/2007 |
| WO | WO-2007/041248 | 4/2007 |
| WO | WO-2007/056638 | 5/2007 |
| WO | WO-2007/065285 | 6/2007 |
| WO | WO-2007/101223 | 9/2007 |
| WO | WO-2007/120363 | 10/2007 |
| WO | WO-2007/126444 | 11/2007 |
| WO | WO-2007/053832 | 12/2007 |
| WO | WO-2007/143225 | 12/2007 |
| WO | WO-2007/149319 | 12/2007 |
| WO | WO-2008/001366 | 1/2008 |
| WO | WO-2008/021913 | 2/2008 |
| WO | WO-2008/042760 | 4/2008 |
| WO | WO-2008/086541 | 7/2008 |
| WO | WO-2008/128210 | 10/2008 |
| WO | WO-2008/130896 | 10/2008 |
| WO | WO-2008/130897 | 10/2008 |
| WO | WO-2008/130898 | 10/2008 |
| WO | WO-2008/143943 | 11/2008 |
| WO | WO-2009/018058 | 2/2009 |
| WO | WO-2009/086216 | 7/2009 |
| WO | WO-2009/096992 | 8/2009 |
| WO | WO-2009/097594 | 8/2009 |
| WO | WO-2010/077329 | 7/2010 |
| WO | WO-2011/104616 | 9/2011 |

OTHER PUBLICATIONS

Aussedat, B., et al., "A User-Friendly Method for Calibrating a Subcutaneous Glucose Sensor-Based Hypoglycemic Alarm", *Biosensors & Bioelectronics*, vol. 12, No. 11, 1997, pp. 1061-1070.

Bennion, N., et al., "Alternate Site Glucose Testing: A Crossover Design", *Diabetes Technology & Therapeutics*, vol. 4 No. 1, 2002, pp. 25-33.

(56) References Cited

OTHER PUBLICATIONS

Blank, T. B., et al., "Clinical Results From a Non-Invasive Blood Glucose Monitor", *Optical and Diagnostics and Sensing of Biological Fluids and Glucose Cholesterol Monitoring II, Proceedings of SPIE*, vol. 4624, 2002, pp. 1-10.
Bremer, T. M., et al., "Benchmark Data from the Literature for Evaluation of New Glucose Sensing Technologies", *Diabetes Technology & Therapeutics*, vol. 3, No. 3, 2001, pp. 409-418.
Brooks, S. L., et al., "Development of an On-Line Glucose Sensor for Fermentation Monitoring", *Biosensors*, vol. 3, 1987/88, pp. 45-56.
Cass, A. E., et al., "Ferrocene-Medicated Enzyme Electrode for Amperometric Determination of Glucose", *Analytical Chemistry*, vol. 56, No. 4, 1984, 667-671.
Cheyne, E. H., et al., "Performance of a Continuous Glucose Monitoring System During Controlled Hypoglycaemia in Healthy Volunteers", *Diabetes Technology & Therapeutics*, vol. 4, No. 5, 2002, pp. 607-613.
Csoregi, E., et al., "Design and Optimization of a Selective Subcutaneously Implantable Glucose Electrode Based on 'Wired' Glucose Oxidase", *Analytical Chemistry*, vol. 67, No. 7, 1995, pp. 1240-1244.
El-Khatib, F. H, et al., "Adaptive Closed-Loop Control Provides Blood-Glucose Regulation Using Subcutaneous Insulin and Glucagon Infusion in Diabetic Swine", *Journal of Diabetes Science and Technology*, vol. 1, No. 2, 2007, pp. 181-192.
Feldman, B., et al., "A Continuous Glucose Sensor Based on Wired Enzyme™ Technology—Results from a 3-Day Trial in Patients with Type 1 Diabetes", *Diabetes Technology & Therapeutics*, vol. 5, No. 5, 2003, pp. 769-779.
Feldman, B., et al., "Correlation of Glucose Concentrations in Interstitial Fluid and Venous Blood During Periods of Rapid Glucose Change", *Abbott Diabetes Care, Inc. Freestyle Navigator Continuous Glucose Monitor Pamphlet*, 2004.
Garg, S., et al., "Improvement in Glycemic Excursions with a Transcutaneous, Real-Time Continuous Glucose Sensor", *Diabetes Care*, vol. 29, No. 1, 2006, pp. 44-50.
Isermann, R., "Supervision, Fault-Detection and Fault-Diagnosis Methods—An Introduction", *Control Engineering Practice*, vol. 5, No. 5, 1997, pp. 639-652.
Isermann, R., et al., "Trends in the Application of Model-Based Fault Detection and Diagnosis of Technical Processes", *Control Engineering Practice*, vol. 5, No. 5, 1997, pp. 709-719.
Johnson, P. C., "Peripheral Circulation", *John Wiley & Sons*, 1978, pp. 198.
Jungheim, K., et al., "How Rapid Does Glucose Concentration Change in Daily Life of Patients with Type 1 Diabetes?", 2002, pp. 250.
Jungheim, K., et al., "Risky Delay of Hypoglycemia Detection by Glucose Monitoring at the Arm", *Diabetes Care*, vol. 24, No. 7, 2001, pp. 1303-1304.
Kaplan, S. M., "Wiley Electrical and Electronics Engineering Dictionary", *IEEE Press*, 2004, pp. 141, 142, 548, 549.
Kuure-Kinsey, M., et al., "A Dual-Rate Kalman Filter for Continuous Glucose Monitoring", *Proceedings of the 28th IEEE, EMBS Annual International Conference*, New York City, 2006, pp. 63-66.
Lo, B., et al., "Key Technical Challenges and Current Implementations of Body Sensor Networks", *Body Sensor Networks*, 2005, pp. 1-5.
Lodwig, V., et al., "Continuous Glucose Monitoring with Glucose Sensors: Calibration and Assessment Criteria", *Diabetes Technology & Therapeutics*, vol. 5, No. 4, 2003, pp. 573-587.
Lortz, J., et al., "What is Bluetooth? We Explain the Newest Short-Range Connectivity Technology", *Smart Computing Learning Series, Wireless Computing*, vol. 8, Issue 5, 2002, pp. 72-74.
Malin, S. F., et al., "Noninvasive Prediction of Glucose by Near-Infrared Diffuse Reflectance Spectroscopy", *Clinical Chemistry*, vol. 45, No. 9, 1999, pp. 1651-1658.
McGarraugh, G., et al., "Glucose Measurements Using Blood Extracted from the Forearm and the Finger", *TheraSense, Inc.*, 2001, 16 Pages.

McGarraugh, G., et al., "Physiological Influences on Off-Finger Glucose Testing", *Diabetes Technology & Therapeutics*, vol. 3, No. 3, 2001, pp. 367-376.
McKean, B. D., et al., "A Telemetry-Instrumentation System for Chronically Implanted Glucose and Oxygen Sensors", *IEEE Transactions on Biomedical Engineering*, vol. 35, No. 7, 1988, pp. 526-532.
Morbiducci, U, et al., "Improved Usability of the Minimal Model of Insulin Sensitivity Based on an Automated Approach and Genetic Algorithms for Parameter Estimation", *Clinical Science*, vol. 112, 2007, pp. 257-263.
Mougiakakou, et al., "A Real Time Simulation Model of Glucose-Insulin Metabolism for Type 1 Diabetes Patients", *Proceedings of the 2005 IEEE*, 2005, pp. 298-301.
Panteleon, A. E., et al., "The Role of the Independent Variable to Glucose Sensor Calibration", *Diabetes Technology & Therapeutics*, vol. 5, No. 3, 2003, pp. 401-410.
Parker, R., et al., "Robust H∞ Glucose Control in Diabetes Using a Physiological Model", *AIChE Journal*, vol. 46, No. 12, 2000, pp. 2537-2549.
Pickup, J., et al., "Implantable Glucose Sensors: Choosing the Appropriate Sensing Strategy", *Biosensors*, vol. 3, 1987/88, pp. 335-346.
Pickup, J., et al., "In Vivo Molecular Sensing in Diabetes Mellitus: An Implantable Glucose Sensor with Direct Electron Transfer", *Diabetologia*, vol. 32, 1989, pp. 213-217.
Pishko, M. V., et al., "Amperometric Glucose Microelectrodes Prepared Through Immobilization of Glucose Oxidase in Redox Hydrogels", *Analytical Chemistry*, vol. 63, No. 20, 1991, pp. 2268-2272.
Quinn, C. P., et al., "Kinetics of Glucose Delivery to Subcutaneous Tissue in Rats Measured with 0.3-mm Amperometric Microsensors", *The American Physiological Society*, 1995, E155-E161.
Rodriguez, N., et al., "Flexible Communication and Control Protocol for Injectable Neuromuscular Interfaces", *IEEE Transactions on Biomedical Circuits and Systems*, vol. 1, No. 1, 2007, pp. 19-27.
Roe, J. N., et al., "Bloodless Glucose Measurements", *Critical Review in Therapeutic Drug Carrier Systems*, vol. 15, Issue 3, 1998, pp. 199-241.
Sakakida, M., et al., "Development of Ferrocene-Mediated Needle-Type Glucose Sensor as a Measure of True Subcutaneous Tissue Glucose Concentrations", *Artificial Organs Today*, vol. 2, No. 2, 1992, pp. 145-158.
Sakakida, M., et al., "Ferrocene-Mediated Needle-Type Glucose Sensor Covered with Newly Designed Biocompatible Membrane", *Sensors and Actuators B*, vol. 13-14, 1993, pp. 319-322.
Salehi, C., et al., "A Telemetry-Instrumentation System for Long-Term Implantable Glucose and Oxygen Sensors", *Analytical Letters*, vol. 29, No. 13, 1996, pp. 2289-2308.
Schmidtke, D. W., et al., "Measurement and Modeling of the Transient Difference Between Blood and Subcutaneous Glucose Concentrations in the Rat After Injection of Insulin", *Proceedings of the National Academy of Sciences*, vol. 95, 1998, pp. 294-299.
Shaw, G. W., et al., "In Vitro Testing of a Simply Constructed, Highly Stable Glucose Sensor Suitable for Implantation in Diabetic Patients", *Biosensors & Bioelectronics*, vol. 6, 1991, pp. 401-406.
Shichiri, M., et al., "Glycaemic Control in Pancreatectomized Dogs with a Wearable Artificial Endocrine Pancreas", *Diabetologia*, vol. 24, 1983, pp. 179-184.
Shichiri, M., et al., "In Vivo Characteristics of Needle-Type Glucose Sensor—Measurements of Subcutaneous Glucose Concentrations in Human Volunteers", *Hormone and Metabolic Research Supplement Series*, vol. 20, 1988, pp. 17-20.
Shichiri, M., et al., "Membrane Design for Extending the Long-Life of an Implantable Glucose Sensor", *Diabetes Nutrition and Metabolism*, vol. 2, 1989, pp. 309-313.
Shichiri, M., et al., "Needle-type Glucose Sensor for Wearable Artificial Endocrine Pancreas", *Implantable Sensors for Closed-Loop Prosthetic Systems, Chapter 15*, 1985, pp. 197-210.
Shichiri, M., et al., "Telemetry Glucose Monitoring Device With Needle-Type Glucose Sensor: A Useful Tool for Blood Glucose Monitoring in Diabetic Individuals", *Diabetes Care*, vol. 9, No. 3, 1986, pp. 298-301.

(56) References Cited

OTHER PUBLICATIONS

Shichiri, M., et al., "Wearable Artificial Endocrine Pancreas With Needle-Type Glucose Sensor", *The Lancet*, 1982, pp. 1129-1131.

Shults, M. C., et al., "A Telemetry-Instrumentation System for Monitoring Multiple Subcutaneously Implanted Glucose Sensors", *IEEE Transactions on Biomedical Engineering*, vol. 41, No. 10, 1994, pp. 937-942.

Sternberg, R., et al., "Study and Development of Multilayer Needle-Type Enzyme-Based Glucose Microsensors", *Biosensors*, vol. 4, 1988, pp. 27-40.

Thompson, M., et al., "In Vivo Probes: Problems and Perspectives", *Clinical Biochemistry*, vol. 19, 1986, pp. 255-261.

Turner, A., et al., "Diabetes Mellitus: Biosensors for Research and Management", *Biosensors*, vol. 1, 1985, pp. 85-115.

Updike, S. J., et al., "Principles of Long-Term Fully Implanted Sensors with Emphasis on Radiotelemetric Monitoring of Blood Glucose from Inside a Subcutaneous Foreign Body Capsule (FBC)", *Biosensors in the Body: Continuous in vivo Monitoring, Chapter 4*, 1997, pp. 117-137.

Velho, G., et al., "Strategies for Calibrating a Subcutaneous Glucose Sensor", *Biomedica Biochimica Acta*, vol. 48, 1989, pp. 957-964.

Wilson, G. S., et al., "Progress Toward the Development of an Implantable Sensor for Glucose", *Clinical Chemistry*, vol. 38, No. 9, 1992, pp. 1613-1617.

PCT Application No. PCT/US2010/044038, International Preliminary Report on Patentability and Written Opinion of the International Searching Authority mailed Feb. 9, 2012.

PCT Application No. PCT/US2010/044038, International Search Report and Written Opinion of the International Searching Authority mailed Sep. 29, 2010.

U.S. Appl. No. 12/848,075, Notice of Allowance mailed Apr. 12, 2013.

U.S. Appl. No. 12/848,075, Office Action mailed Nov. 2, 2012.

\* cited by examiner

METHOD AND APPARATUS FOR PROVIDING ANALYTE MONITORING SYSTEM CALIBRATION ACCURACY

RELATED APPLICATION

The present application is a continuation of U.S. patent application Ser. No. 12/848,075 filed Jul. 30, 2010, now U.S. Pat. No. 8,478,557, which claims priority under 35 U.S.C. §119(e) to U.S. provisional application No. 61/230,686 filed Jul. 31, 2009, entitled "Method and Apparatus for Providing Analyte Monitoring System Calibration Accuracy", the disclosures of each of which are incorporated herein by reference for all purposes.

BACKGROUND

As is known, Type-1 diabetes mellitus condition exists when the beta cells ((($\beta$-cells) which produce insulin to counteract the rise in glucose levels in the blood stream) in the pancreas either die or are unable to produce a sufficient amount of insulin naturally in response to elevated glucose levels. It is increasingly common for patients diagnosed with diabetic conditions to monitor their blood glucose levels using commercially available continuous glucose monitoring systems to take timely corrective actions. Some monitoring systems use sensors that require periodic calibration using a reference glucose measurement (for example, using an in vitro test strip). The FreeStyle Navigator® Continuous Glucose Monitoring System available from Abbott Diabetes Care Inc., of Alameda, Calif. is a continuous glucose monitoring system that provides the user with real time glucose level information. Using the continuous glucose monitoring system, for example, diabetics are able to determine when insulin is needed to lower glucose levels or when additional glucose is needed to raise the level of glucose.

Further, typical treatment of Type-1 diabetes includes the use of insulin pumps that are programmed for continuous delivery of insulin to the body through an infusion set. The use of insulin pumps to treat Type-2 diabetes (where the beta cells in the pancreas do produce insulin, but an inadequate quantity) has also become more prevalent. Such insulin delivery devices are preprogrammed with delivery rates such as basal profiles which are tailored to each user, and configured to provide the needed insulin to the user. In addition, continuous glucose monitoring systems have been developed to allow real time monitoring of fluctuation in glucose levels.

When the insulin delivery system and the glucose monitoring system are used separately, used together, or integrated into a single system, for example, in a single semi-closed loop or closed loop therapy system, the administered insulin (as well as other parameters or conditions) may affect some functions associated with the glucose monitoring system.

SUMMARY

In view of the foregoing, in aspects of the present disclosure, there are provided methods and apparatus for improving accuracy of the continuous glucose monitoring system calibration based at least in part on the insulin delivery information, and parameters associated with the administration of insulin.

Also provided are systems and kits.

INCORPORATION BY REFERENCE

The following patents, applications and/or publications are incorporated herein by reference for all purposes: U.S. Pat. Nos. 4,545,382; 4,711,245; 5,262,035; 5,262,305; 5,264,104; 5,320,715; 5,356,786; 5,509,410; 5,543,326; 5,593,852; 5,601,435; 5,628,890; 5,820,551; 5,822,715; 5,899,855; 5,918,603; 6,071,391; 6,103,033; 6,120,676; 6,121,009; 6,134,461; 6,143,164; 6,144,837; 6,161,095; 6,175,752; 6,270,455; 6,284,478; 6,299,757; 6,338,790; 6,377,894; 6,461,496; 6,503,381; 6,514,460; 6,514,718; 6,540,891; 6,560,471; 6,579,690; 6,591,125; 6,592,745; 6,600,997; 6,605,200; 6,605,201; 6,616,819; 6,618,934; 6,650,471; 6,654,625; 6,676,816; 6,730,200; 6,736,957; 6,746,582; 6,749,740; 6,764,581; 6,773,671; 6,881,551; 6,893,545; 6,932,892; 6,932,894; 6,942,518; 7,041,468; 7,167,818; and 7,299,082; U.S. Published Application Nos. 2004/0186365; 2005/0182306; 2006/0025662; 2006/0091006; 2007/0056858; 2007/0068807; 2007/0095661; 2007/0108048; 2007/0199818; 2007/0227911; 2007/0233013; 2008/0066305; 2008/0081977; 2008/0102441; 2008/0148873; 2008/0161666; 2008/0267823; and 2009/0054748; U.S. patent application Ser. Nos. 11/461,725; 12/131,012; 12/242,823; 12/363,712; 12/495,709; 12/698,124; 12/698,129; 12/714,439; 12/794,721; and 12/842,013; U.S. Provisional Application Ser. No. 61/347,754.

DETAILED DESCRIPTION

Figure 1:
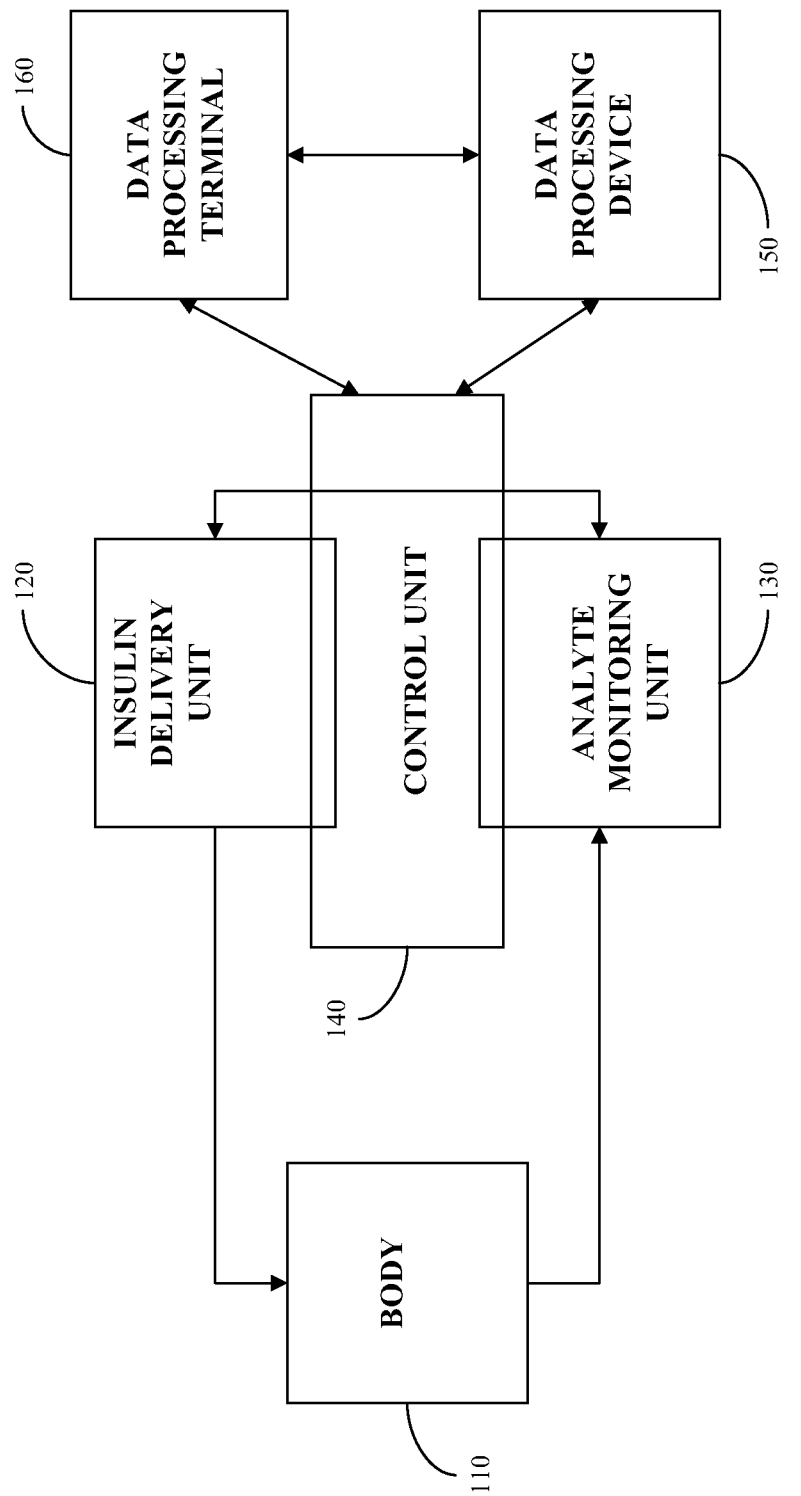
FIG. 1 is a block diagram illustrating an overall system in accordance with one embodiment of the present disclosure.

Before embodiments of the present disclosure are described, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges is also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described. All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise.

The publications discussed herein are provided solely for their disclosure prior to the filing date of the present application. Nothing herein is to be construed as an admission that the present disclosure is not entitled to antedate such publication by virtue of prior disclosure. Further, the dates of publication provided may be different from the actual publication dates which may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure.

The figures shown herein are not necessarily drawn to scale, with some components and features being exaggerated for clarity.

Generally, embodiments of the present disclosure relate to methods and system for providing improved analyte sensor calibration accuracy based at least in part on the insulin delivery information. In certain embodiments, the present disclosure relates to the continuous and/or automatic in vivo monitoring of the level of an analyte using an analyte sensor, and under one or more control algorithms, determines appropriate or suitable conditions for performing calibration of the analyte sensor in view of the scheduled delivery of insulin or administered insulin amount. While the calibration accuracy of the analyte sensor is discussed in conjunction with the insulin delivery information, one or more other parameters or conditions may be incorporated to improve the calibration accuracy including, for example but not limited to, the physiological model associated with the patient using the analyte sensor, meal information, exercise information, activity information, disease information, and historical physiological condition information.

Embodiments include medication delivery devices such as external infusion pumps, implantable infusion pumps, on-body patch pumps, or any other processor controlled medication delivery devices that are in communication with one or more control units which also control the operation of the analyte monitoring devices. The medication delivery devices may include one or more reservoirs or containers to hold the medication for delivery in fluid connection with an infusion set, for example, including an infusion tubing and/or cannula. The cannula may be positioned so that the medication is delivered to the user or patient at a desired location, such as, for example, in the subcutaneous tissue under the skin layer of the user.

Embodiments include analyte monitoring devices and systems that include an analyte sensor, at least a portion of which is positionable beneath the skin of the user, for the in vivo detection of an analyte, such as glucose, lactate, and the like, in a body fluid. Embodiments include wholly implantable analyte sensors and analyte sensors in which only a portion of the sensor is positioned under the skin and a portion of the sensor resides above the skin, e.g., for contact to a transmitter, receiver, transceiver, processor, etc.

A sensor (and/or a sensor insertion apparatus) may be, for example, configured to be positionable in a patient for the continuous or periodic monitoring of a level of an analyte in a patient's dermal fluid. For the purposes of this description, continuous monitoring and periodic monitoring will be used interchangeably, unless noted otherwise.

The analyte level may be correlated and/or converted to analyte levels in blood or other fluids. In certain embodiments, an analyte sensor may be configured to be positioned in contact with dermal fluid to detect the level of glucose, which detected glucose may be used to infer the glucose level in the patient's bloodstream. For example, analyte sensors may be insertable through the skin layer and into the dermal layer under the skin surface at a depth of approximately 3 mm under the skin surface and containing dermal fluid. Embodiments of the analyte sensors of the subject disclosure may be configured for monitoring the level of the analyte over a time period which may range from minutes, hours, days, weeks, months, or longer.

Of interest are analyte sensors, such as glucose sensors, that are capable of in vivo detection of an analyte for about one hour or more, e.g., about a few hours or more, e.g., about a few days of more, e.g., about three or more days, e.g., about five days or more, e.g., about seven days or more, e.g., about several weeks or at least one month. Future analyte levels may be predicted based on information obtained, e.g., the current analyte level at time, the rate of change of the analyte, etc. Predictive alarms may notify the control unit (and/or the user) of predicted analyte levels that may be of concern in advance of the analyte level reaching the future level. This enables the control unit to determine a priori a suitable corrective action and implement such corrective action.

FIG. 1 is a block diagram illustrating an overall system in accordance with one embodiment of the present disclosure. Referring to FIG. 1, in one aspect, the system 100 includes an insulin delivery unit 120 that is connected to a body 110 of a user or patient to establish a fluid path to deliver medication such as insulin. In one aspect, the insulin delivery unit 120 may include an infusion tubing fluidly connecting the reservoir of the delivery unit 120 to the body 110 using a cannula with a portion thereof positioned in the subcutaneous tissue of the body 110.

Referring to FIG. 1, the system 100 also includes an analyte monitoring unit 130 that is configured to monitor the analyte level in the body 110. As shown in FIG. 1, a control unit 140 is provided to control the operation of the insulin delivery unit 120 and the analyte monitoring unit 130. In one embodiment, the control unit 140 may be a processor based control unit having provided therein one or more control algorithms to control the operation of the analyte monitoring unit 130 and the delivery unit 120. In one aspect, the control unit 140, the analyte monitoring unit 130 and the delivery unit 120 may be integrated in a single housing. In other embodiments, the control unit 140 may be provided in the housing of the delivery unit 120 and configured for communication (wireless or wired) with the analyte monitoring unit 130. In an alternate embodiment, the control unit may be integrated in the housing of the analyte monitoring unit 130 and configured for communication (wireless or wired) with the delivery unit 120. In yet another embodiment, the control unit 140 may be a separate component of the overall system 100 and configured for communication (wireless or wired) with both the delivery unit 120 and the analyte monitoring unit 130.

Referring back to FIG. 1, the analyte monitoring unit 130 may include an analyte sensor that is transcutaneously positioned through a skin layer of the body 110, and is in signal communication with a compact data transmitter provided on the skin layer of the body 110 which is configured to transmit the monitored analyte level substantially in real time to the analyte monitoring unit 130 for processing and/or display. In another aspect, the analyte sensor may be wholly implantable in the body 110 with a data transmitter and configured to wirelessly transmit the monitored analyte level to the analyte monitoring unit 130.

Referring still to FIG. 1, also shown in the overall system 100 is a data processing device 150 in signal communication with the one or more of the control unit 140, delivery unit 120 and the analyte monitoring unit 130. In one aspect, the data processing device 150 may include an optional or supplemental device in the overall system 100 to provide user input/output functions, data storage and processing. Examples of the data processing device 150 include, but are not limited to mobile telephones, personal digital assistants (PDAs), in vitro blood glucose meters, smart phone devices including Blackberry® devices, iPhone® devices, and Palm® devices, data paging devices, and the like, each of which include an output unit such as one or more of a display, audible and/or vibratory output, and/or an input unit such as a keypad, keyboard, input buttons and the like, and which are configured for communication (wired or wireless) to receive and/or transmit data, and further, which include memory devices such as random access memory, read only memory, volatile and/or non-volatile memory that store data.

Also shown in the overall system 100 is a data processing terminal 160 which may include a personal computer, a server terminal, a laptop computer, a handheld computing device, or other similar computing devices that are configured for data communication (over the internet, local area network (LAN), cellular network and the like) with the one or more of the control unit 140, the delivery unit 120, the analyte monitoring unit 130, and the data processing device 150, to process, analyze, store, archive, and update information.

It is to be understood that the analyte monitoring unit 130 of FIG. 1 may be configured to monitor a variety of analytes at the same time or at different times. Analytes that may be monitored include, but are not limited to, acetyl choline, amylase, bilirubin, cholesterol, chorionic gonadotropin, creatine kinase (e.g., CK-MB), creatine, DNA, fructosamine, glucose, glutamine, growth hormones, hormones, ketones, lactate, peroxide, prostate-specific antigen, prothrombin, RNA, thyroid stimulating hormone, and troponin. The concentration of drugs, such as, for example, antibiotics (e.g., gentamicin, vancomycin, and the like), digitoxin, digoxin, drugs of abuse, theophylline, and warfarin, may also be monitored. In those embodiments that monitor more than one analyte, the analytes may be monitored at the same or different times.

Additional detailed descriptions of embodiments of the continuous analyte monitoring device and system, calibrations protocols, embodiments of its various components are provided in, among others, U.S. Pat. Nos. 6,175,752, 6,284,478, 7,299,082 and U.S. patent application Ser. No. 10/745,878 filed Dec. 26, 2003 entitled "Continuous Glucose Monitoring System and Methods of Use", the disclosures of each of which are incorporated herein by reference in their entirety for all purposes. Additional detailed description of systems including medication delivery units and analyte monitoring devices, embodiments of the various components are provided in, among others, U.S. patent application Ser. No. 11/386,915, entitled "Method and System for Providing Integrated Medication Infusion and Analyte Monitoring System", the disclosure of which is incorporated herein by reference for all purposes. Moreover, additional detailed description of medication delivery devices and components are provided in, among others, U.S. Pat. No. 6,916,159, the disclosure of which is incorporated herein by reference for all purposes.

Referring back to FIG. 1, each of the components shown in the system 100 may be configured to be uniquely identified by one or more of the other components in the system so that communication conflict may be readily resolved between the various components, for example, by exchanging or pre-storing and/or verifying unique device identifiers as part of communication between the devices, by using periodic keep alive signals, or configuration of one or more devices or units in the overall system as a master-slave arrangement with periodic bi-directional communication to confirm integrity of signal communication therebetween.

Further, data communication may be encrypted or encoded (and subsequently decoded by the device or unit receiving the data), or transmitted using public-private keys, to ensure integrity of data exchange. Also, error detection and/or correction using, for example, cyclic redundancy check (CRC) or techniques may be used to detect and/or correct for errors in signals received and/or transmitted between the devices or units in the system 100. In certain aspects, data communication may be responsive to a command or data request received from another device in the system 100, while some aspects of the overall system 100 may be configured to periodically transmit data without prompting, such as the data transmitter, for example, in the analyte monitoring unit 130 periodically transmitting analyte related signals.

In certain embodiments, the communication between the devices or units in the system 100 may include one or more of an RF communication protocol, an infrared communication protocol, a Bluetooth® enabled communication protocol, an 802.11x wireless communication protocol, internet connection over a data network or an equivalent wireless communication protocol which would allow secure, wireless communication of several units (for example, per HIPAA requirements) while avoiding potential data collision and interference.

In certain embodiments, data processing device 150, analyte monitoring unit 130 and/or delivery unit 120 may include blood glucose meter functions or capability to receive blood glucose measurements which may be used, for example to calibrate the analyte sensor. For example, the housing of these devices may include a strip port to receive a blood glucose test strip with blood sample to determine the blood glucose level. Alternatively, a user input device such as an input button or keypad may be provided to manually enter such information.

Still further, upon completion of a blood glucose measurement, the result may be wirelessly and/or automatically transmitted to another device in the system 100. For example, it is desirable to maintain a certain level of water tight seal on the housing of the delivery unit 120 during continuous use by the patient or user. In such case, incorporating a strip port to receive a blood glucose test strip may be undesirable. As such, the blood glucose meter function including the strip port may be integrated in the housing of another one of the devices or units in the system (such as in the analyte monitoring unit 130 and/or data processing device 150). In this case, the result from the blood glucose test, upon completion may be wirelessly transmitted to the delivery unit 120 for storage and further processing.

Any suitable test strip may be employed, e.g., test strips that only require a very small amount (e.g., one microliter or less, e.g., 0.5 microliter or less, e.g., 0.1 microliter or less), of applied sample to the strip in order to obtain accurate glucose information, e.g. Freestyle® or Precision® blood glucose test strips from Abbott Diabetes Care Inc. Glucose information obtained by the in vitro glucose testing device may be used for a variety of purposes, computations, etc. For example, the information may be used to calibrate the analyte sensor, confirm results of the sensor to increase the confidence in the accuracy level thereof (e.g., in instances in which information obtained by sensor is employed in therapy related decisions), determine suitable amount of bolus dosage for administration by the delivery unit 120.

In certain embodiments, a sensor may be calibrated using only one sample of body fluid per calibration event. For example, a user need only lance a body part one time to obtain sample for a calibration event (e.g., for a test strip), or may lance more than one time within a short period of time if an insufficient volume of sample is obtained firstly. Embodiments include obtaining and using multiple samples of body fluid for a given calibration event, where glucose values of each sample are substantially similar. Data obtained from a given calibration event may be used independently to calibrate or combined with data obtained from previous calibration events, e.g., averaged including weighted averaged, etc., to calibrate.

One or more devices or components of the system 100 may include an alarm system that, e.g., based on information from control unit 140, warns the patient of a potentially detrimental condition of the analyte. For example, if glucose is the analyte, an alarm system may warn a user of conditions such as hypoglycemia and/or hyperglycemia and/or impending hypoglycemia, and/or impending hyperglycemia. An alarm system may be triggered when analyte levels reach or exceed a threshold value. An alarm system may also, or alternatively, be activated when the rate of change or acceleration of the rate of change in analyte level increase or decrease reaches or exceeds a threshold rate of change or acceleration. For example, in the case of the glucose monitoring unit 130, an alarm system may be activated if the rate of change in glucose concentration exceeds a threshold value which might indicate that a hyperglycemic or hypoglycemic condition is likely to occur. In the case of the delivery unit 120, alarms may be associated with occlusion conditions, low reservoir conditions, malfunction or anomaly in the fluid delivery and the like. System alarms may also notify a user of system information such as battery condition, calibration, sensor dislodgment, sensor malfunction, etc. Alarms may be, for example, auditory and/or visual. Other sensory-stimulating alarm systems may be used including alarm systems which heat, cool, vibrate, or produce a mild electrical shock when activated.

Referring yet again to FIG. 1, the control unit 140 of the system 100 may include one or more processors such as microprocessors and/or application specific integrated circuits (ASIC), volatile and/or non-volatile memory devices, and additional components that are configured to store and execute one or more control algorithms to dynamically control the operation of the delivery unit 120 and the analyte monitoring unit 130. The one or more closed loop control algorithms may be stored as a set of instructions in the one or more memory devices and executed by the one or more processors to vary the insulin delivery level based on, for example, glucose level information received from the analyte sensor.

An exemplary model describing the blood-to-interstitial glucose dynamics taking into account of insulin information is described below. More specifically, the model described herein provides for specific elaboration of model-based improvements discussed below. The example provided herein is based on a particular blood-to-interstitial glucose model, and while other models may result in a different particular relationship and parameter set, the underlying concepts and related description remain equally applicable.

Provided below is a model of blood-to-interstitial glucose as described by Wilinska et al. (Wilinska, Bodenlenz, Chassin, Schaller, Schaupp, Pieber, and Hovorka, "*Interstitial Glucose Kinetics in Subjects With Type 1 Diabetes Under Physiologic Conditions*", Metabolism, v. 53 n. 11, November 2004, pp 1484-1492, the disclosure of which is incorporated herein by reference), where interstitial glucose dynamics comprises of a zero order removal of glucose from interstitial fluid $F_{o2}$, a constant decay rate constant $k_{o2}$, a constant glucose transport coefficient $k_{21}$, and an insulin dependent glucose transport coefficient $k_i$.

$$\dot{g}_i(t) = -k_{o2}g_i(t) + [k_{21} + [k_i[I(t) - I_b]]]g_b(t) - F_{o2} \tag{1}$$

where $g_i$ corresponds to interstitial glucose, $g_b$ corresponds to blood glucose, the dot corresponds to the rate of change operation, (t) refers to variables that change over time as opposed to relatively static aforementioned coefficients, I corresponds to insulin concentration at any given time, and $I_b$ corresponds to the steady-state insulin concentration required to maintain a net hepatic glucose balance.

It should be noted that the blood-to-interstitial glucose model described above is affected by insulin and accordingly, factoring in the insulin information will provide improvement to the sensor sensitivity determination.

The determination of insulin concentration (I) and the steady state insulin concentration required to maintain a net hepatic glucose balance ($I_b$) as shown in Equation (1) above may be achieved using insulin dosing history and an insulin pharmacokinetic and pharmacodynamic model. For example, based on a three compartment model of subcutaneous insulin dynamics into plasma insulin I as described by Hovorka, et al. (Hovorka, Canonico, Chassin, Haueter, Massi-Benedetti, Federici, Pieber, Schaller, Schaupp, Vering and Wilinska, "*Nonlinear model predictive control of glucose concentration in subjects with type* 1 *diabetes*", Physiological Measurement, v. 25, 2004, pp 905-920, the disclosure of which is incorporated herein by reference):

$$\dot{I}_1(t) = -k_a I_1(t) + u_{sc}(t) \tag{2}$$
$$\dot{I}_2(t) = -k_a I_2(t) + k_a I_1(t)$$
$$\dot{I}(t) = -k_e I(t) + \frac{k_a}{V} I_2(t)$$

where $I_1$ and $I_2$ are internal insulin compartments that describe the pathway from subcutaneous insulin injection into the plasma insulin compartment I. $I_b$ is calculated by taking the steady-state average of I over a finite window of past and present period. The coefficients $k_a$ and $k_e$ describe the various decay and transport rates of the compartments, and V is the plasma insulin volume. Insulin action time is related to the parameter $k_a$. The input $u_{sc}$ to this model is described in terms of subcutaneous insulin infusion rate. Insulin dose/bolus may be converted into its delivery rate equivalent by monitoring or estimating the actual amount of bolus amount/dose delivered after every regular intervals of time (e.g. by monitoring of the amount of bolus/dose delivered every minute for a given executed bolus dose delivery).

For analyte monitoring systems, an uncalibrated sensor measurement $y_{CGM}$ is related to the true interstitial glucose by the following equation:

$$y_{CGM}(t)=S[g_i(t)+v_i(t)] \quad (3)$$

where S is the calibration sensitivity to be identified, and $v_i$ is sensor noise.

Further, reference blood glucose measurement $y_{BG}$ when available at certain times, such as when requested for calibration at time $t_o$, contaminated by measurement error $v_b$ may be expressed as follows:

$$y_{BG}(t_o)=g_b(t_o)+v_b(t_o) \quad (4)$$

Accordingly, the models and functional relationships described above provide some exemplary system components for providing improvement to the calibration accuracy in analyte monitoring systems whether used as a standalone system, or in conjunction with a medication delivery system such as with an insulin pump.

Determination of the suitable or appropriate time period to perform sensor calibration routine may be accomplished in several manners within the scope of the present disclosure. In one aspect, the calibration schedule may be predetermined or preset based on the initial sensor insertion or positioning in the patient or alternatively, scheduled based on each prior successful calibration event on a relative time basis. In some aspects, calibration routines are delayed or cancelled during high rates of glucose fluctuation because physiological lag between interstitial glucose measured by the analyte sensor and the blood glucose measured by discrete in vitro test strips may result in an error in the sensor sensitivity estimation.

In one aspect, calibration routine or function may be prevented or rejected when the interstitial glucose absolute rate of change is determined to exceed a predetermined threshold level. As the interstitial glucose level generally lags blood glucose level, there may be time periods where the blood glucose may be changing rapidly while the measured interstitial glucose level may not report similar fluctuations—it would change rapidly at some later, lagged time period. In such a case, a lag error may be introduced to the sensitivity determination. Accordingly, in one aspect, the execution of the calibration routine may be delayed or postponed when a sensor calibration request is detected by the system 100 during a time period when an insulin dose of sufficient magnitude is delivered, which may cause the rapid change in blood glucose to occur without a rapid change of interstitial glucose at that instance.

Figure 2:
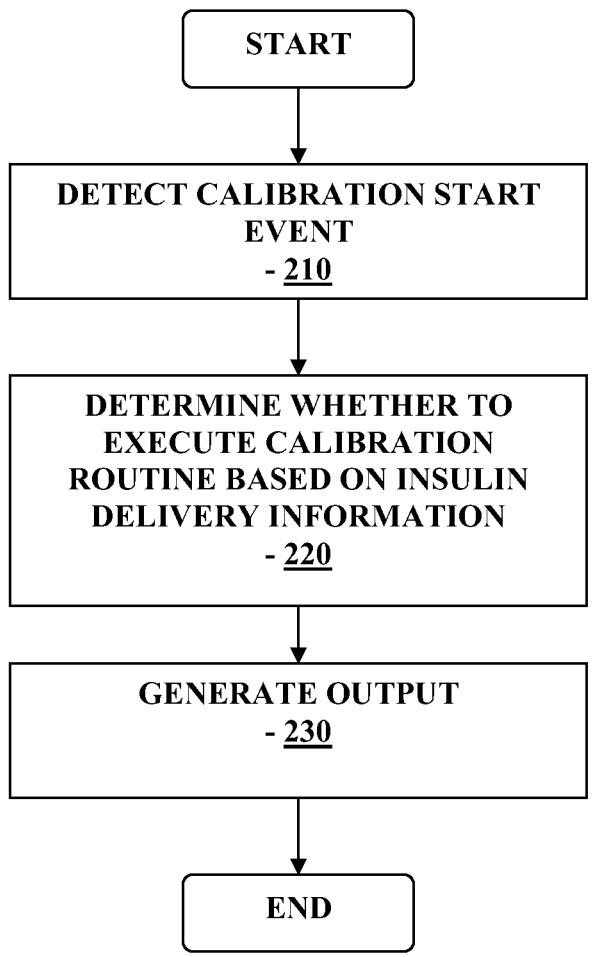
FIG. 2 is a flowchart illustrating calibration accuracy improvement routine in one aspect of the present disclosure.

Referring now to the Figures, FIG. 2 is a flowchart illustrating overall calibration accuracy improvement routine in one aspect of the present disclosure. Referring to FIG. 2, when calibration start event is detected (210), for example, based on a predetermined calibration schedule from sensor insertion, or in response to a user calibration function initiation or execution, it is determined whether the initiated calibration routine is to be executed based on, for example, insulin information (220). Thereafter, one or more data or information associated with the determination is used to generate an output (230) which may, in one aspect, be provided to the user and/or stored in the system 100 (FIG. 1).

Figure 3:
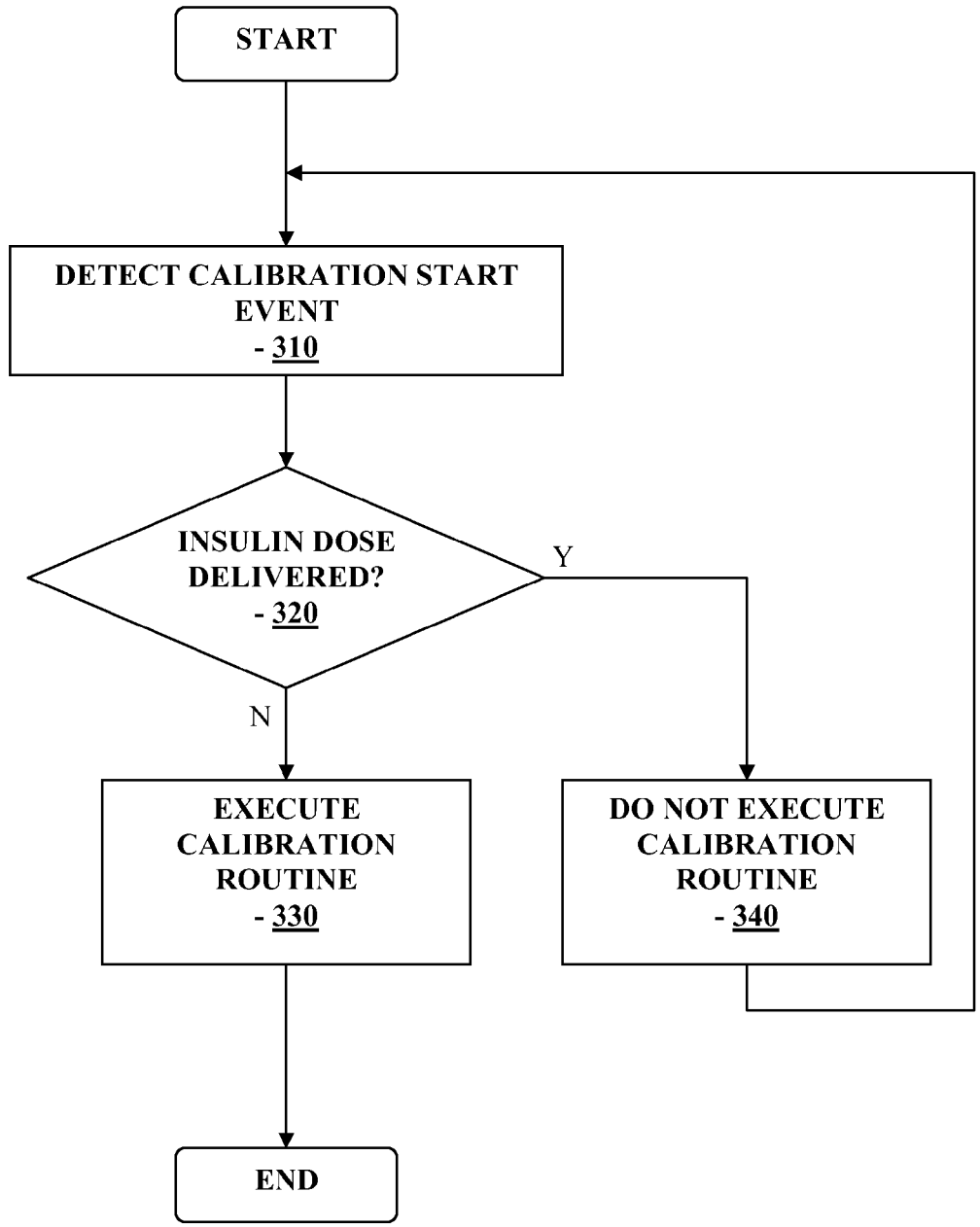
FIG. 3 is a flowchart illustrating calibration accuracy improvement routine in another aspect of the present disclosure.

FIG. 3 is a flowchart illustrating calibration accuracy improvement routine in another aspect of the present disclosure. As shown, when the calibration start event is detected (310), it is determined whether an insulin dose (for example, a bolus amount such as a carbohydrate bolus, or a correction bolus dose) was delivered or administered to the patient (320). In one aspect, as part of determining whether the insulin dose was delivered, it may be also determined whether the insulin dose was delivered within a time period measured from the detected calibration start event (and further, optionally, whether the determined insulin dose delivered amount meets a predetermined threshold level of insulin).

Referring again to FIG. 3, if it is determined that the insulin dose was delivered, then the routine proceeds to step 340 where the initiated calibration routine is not executed, and the routine returns to the beginning and awaits for the detection of the next or subsequent calibration start event. On the other hand, if at step 320 it is determined that the insulin dose was not delivered, then at step 330, the initiated calibration routine is executed to determine, for example, the corresponding sensor sensitivity based on a contemporaneously determined reference measurement (e.g., blood glucose measurement from an in vitro test strip, or another sensor data point that may be used as reference measurement) to calibrate the sensor.

Figure 4:
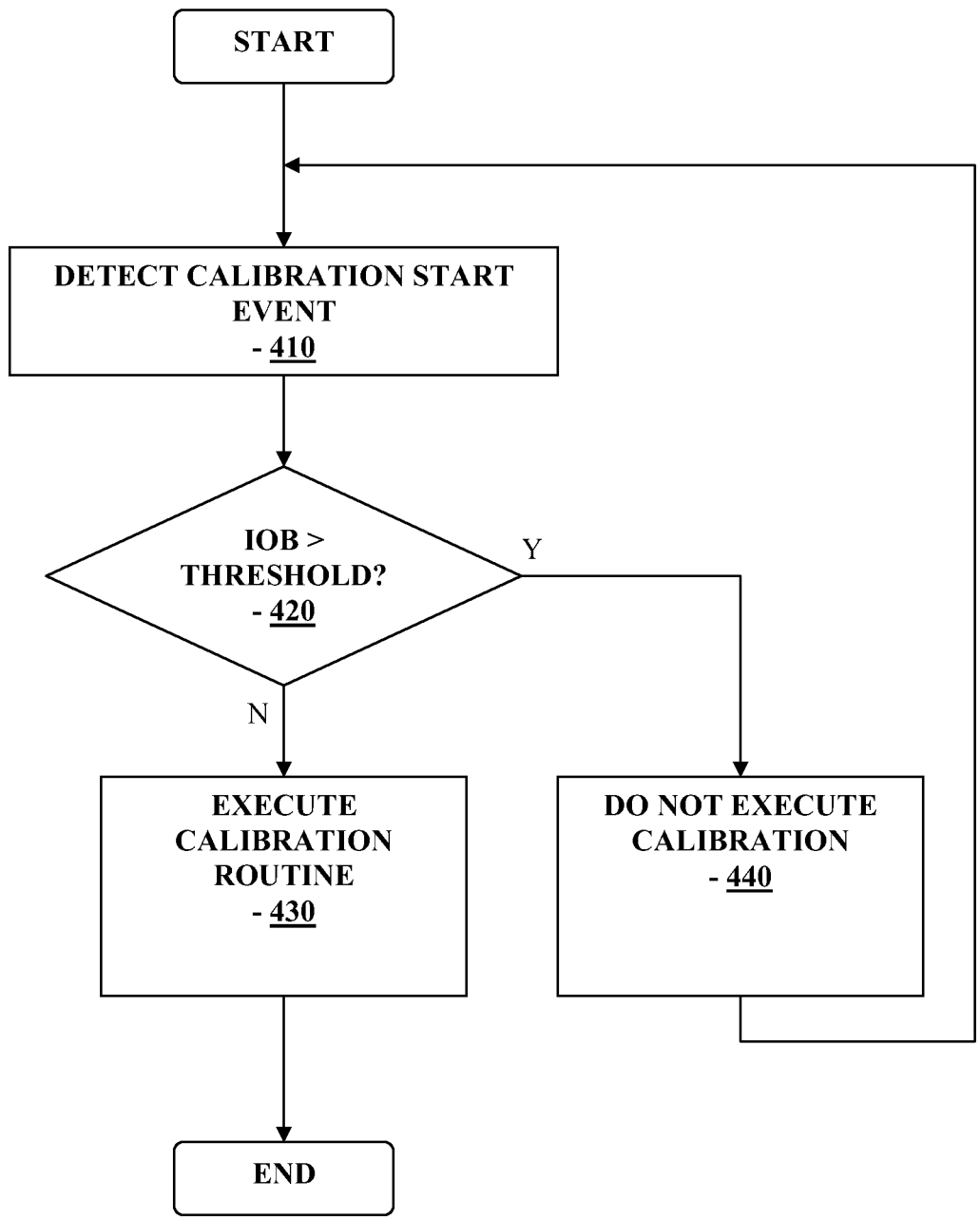
FIG. 4 is a flowchart illustrating calibration accuracy improvement routine in another aspect of the present disclosure.

FIG. 4 is a flowchart illustrating calibration accuracy improvement routine in another aspect of the present disclosure. Referring to FIG. 4, in the embodiment shown, when the calibration start event is detected (410) it is determined whether the insulin on board (IOB) level exceeds a predetermined threshold level (420). That is, in one aspect, the control algorithm may be configured to determine, in response to the detection of a calibration routine initialization, the IOB level. In one aspect, if it is determined that the IOB level exceeds the predetermined threshold level, then the initiated calibration routine is not contemporaneously executed (440), but rather, the called routine may be delayed, postponed, or cancelled, and the routine returns to the beginning to detect the subsequent calibration start event.

Referring to FIG. 4, if on the other hand it is determined that the IOB level is not greater than the predetermined threshold level at step 420, then the initiated calibration routine is executed at step 430 (530 (FIG. 5)), as discussed above, for example, to determine the corresponding analyte sensor sensitivity based on one or more reference glucose measurements to calibrate the sensor data.

Figure 5:
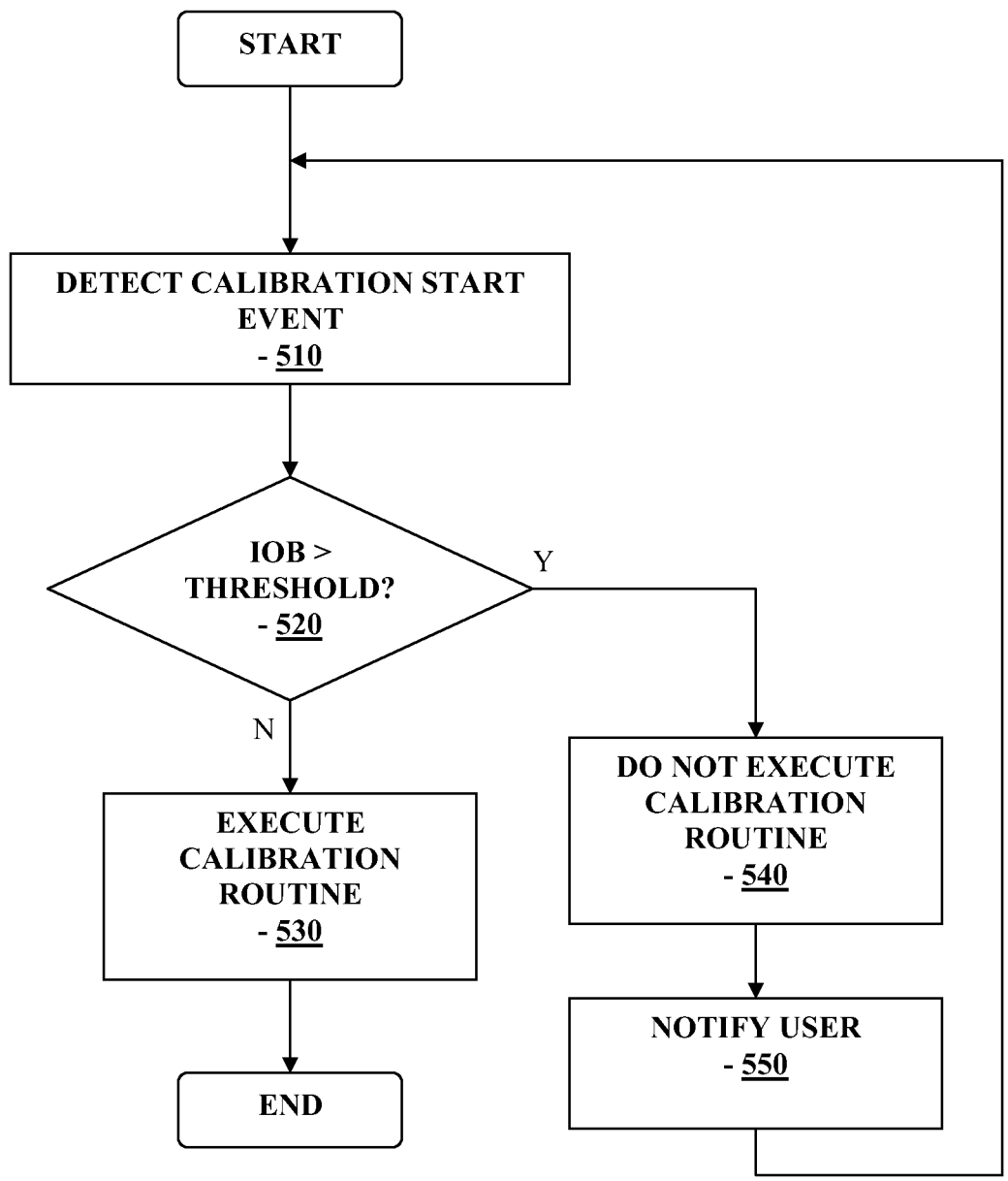
FIG. 5 is a flowchart illustrating calibration accuracy improvement routine in another aspect of the present disclosure.

FIG. 5 is a flowchart illustrating calibration accuracy improvement routine in another aspect of the present disclosure. Compared to the embodiment described in conjunction with FIG. 4, in the embodiment shown in FIG. 5, when the IOB level is determined to exceed the predetermined threshold level (520), then again, the initiated calibration routine is not executed (540), but prior to returning to the beginning of the routine to detect the subsequent calibration start event (510), a user notification function is called to notify the user of a failed (or delayed/postponed) calibration event (550). Such notification may include one or more of a visual indication, an audible indication, a vibratory indication, or one or more combinations thereof.

Figure 6:
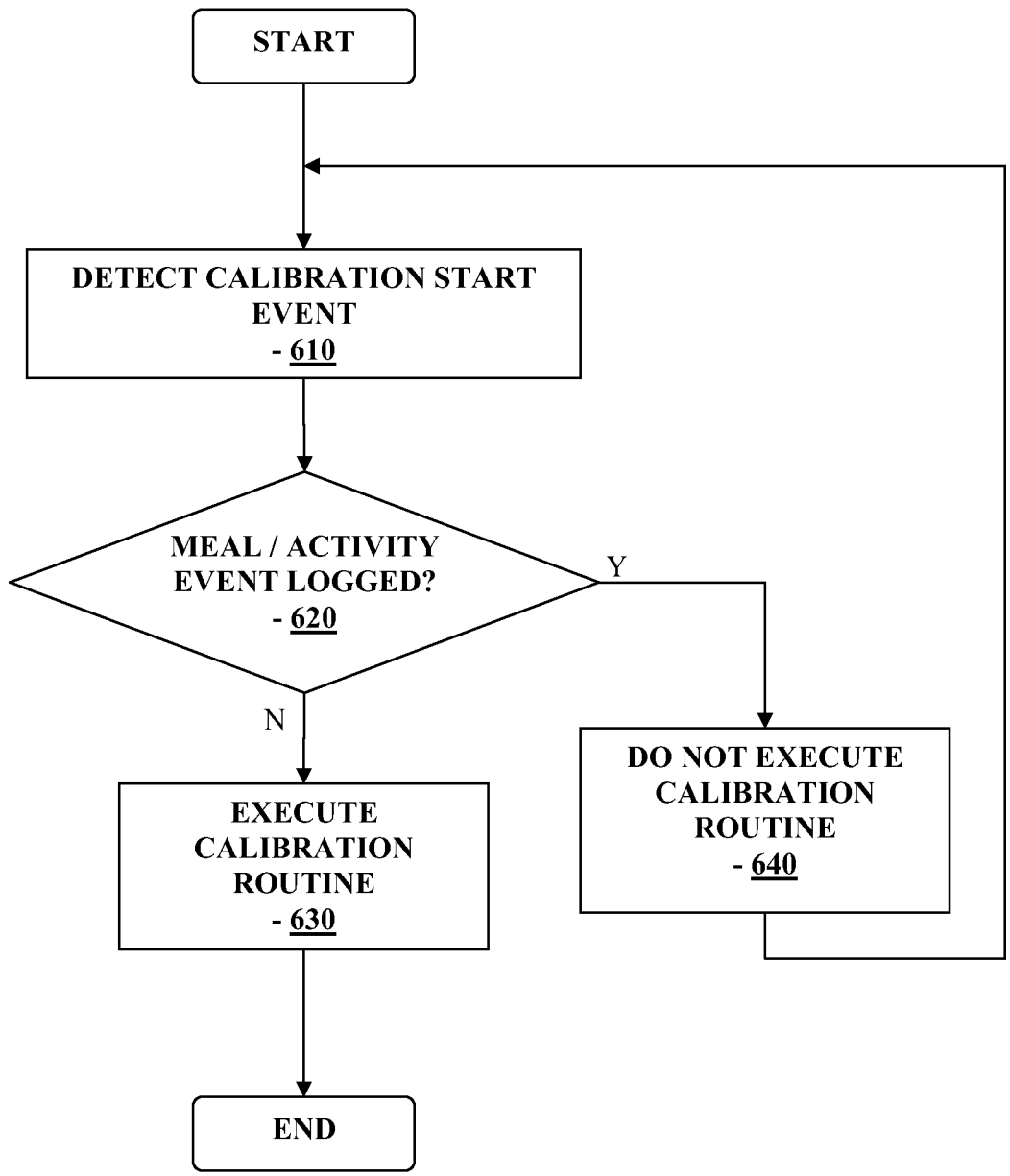
FIG. 6 is a flowchart illustrating calibration accuracy improvement routine in another aspect of the present disclosure.

FIG. 6 is a flowchart illustrating calibration accuracy improvement routine in another aspect of the present disclosure. Referring to FIG. 6, in a further aspect of the present disclosure, when a calibration start event such as the initialization of a scheduled calibration routine is detected (610), it is determined whether a predetermined or categorized event has been logged at step 620. In particular, the control algorithm may be configured to determine whether an event such as a meal event, an activity event, an exercise event, or any other suitable or classified event has been logged at step 620. As discussed above, in one aspect, the control algorithm may be configured to additionally determine the time period of when such event was logged, if any, to determine whether the determined time period falls within a relevant time period with respect to the initiated calibration routine.

For example, if the logged meal event occurred with sufficient temporal distance relative to the initiated calibration routine, that it likely will have minimal relevance, if any to the calibration accuracy associated with the analyte sensor, then such logged event may be ignored. Alternatively, with each retrieved logged event at step 620, the routine may be configured to determine whether the logged event occurred within a specified or predetermined time period, in which case, the routine proceeds to step 640 where the initiated calibration routine is not executed and/or postponed or delayed. As further shown in FIG. 6, the routine thereafter returns to the beginning and monitors the system to determine whether a subsequent calibration start event is detected.

Referring back to FIG. 6, if at step 620 there are no events logged which are classified or categorized as relevant or associated with a parameter that is considered to be relevant, or alternatively, the one or more logged events detected or retrieved fall outside of the predetermined relevant time period (for example, within one hour prior to the calibration start event detected), then the initiated calibration routine proceeds at step 630 and is executed to determine, for example, the sensitivity associated with the analyte sensor based, for example, on a received reference blood glucose measurement, to calibrate the sensor data.

In aspects of the present disclosure, the duration and/or threshold described may be determined based on parameters including, for example, but not limited to insulin sensitivity, insulin action time, time of day, analyte sensor measured glucose level, glucose rate of change, and the like.

Moreover, in aspects of the present disclosure, as discussed, if the condition described above is detected, rather instead of delaying or postponing the execution of the calibration routine, the sensitivity determination may be altered as described in further detail below. That is, in one aspect, a correction factor may be applied to the sensitivity determination based on the insulin dose amount, elapsed time since the administration of the insulin dose, insulin sensitivity and insulin action time, for example. In one aspect, the correction factor may be a predetermined value or parameter, for example, based in part on the model applied to the patient's physiological condition, or may be a factor that is configured to be dynamically updated in accordance with the variation in the monitored parameters such as those described above.

In a further aspect, a glucose model of a patient may be used to predict or determine future glucose (blood and/or interstitial) levels and to estimate present glucose levels (blood and/or interstitial). More specifically, in aspects of the present disclosure, the model applied may also be used to estimate a rate-of-change of these variables and higher order moments of these variables in addition to statistical error estimates (for example, uncertainty estimates).

As discussed, the insulin delivery information and the measured glucose data from the analyte sensor (e.g., multiple measurements of each in time) are two of many input parameters used in conjunction with the embodiments described herein. Accordingly, in one aspect, the calibration routine may be configured to use the predicted output(s) as a check or verification to determine if the calibration routine should be postponed or delayed. For example, if the rate of change of blood glucose is determined to exceed a predetermined threshold, the calibration routine may be postponed or delayed for a predetermined time period. Alternatively, in a further aspect, if it is determined that the uncertainty in the interstitial estimate exceeds a predetermined threshold, the calibration routine may be configured to be postponed or delayed for a predetermined time period. The predetermined time period for a delayed or postponed calibration routine may be a preset time period, or alternatively, dynamically modified based on, for example, but not limited to the level of determined uncertainly in the interstitial estimate, the level of the predetermined threshold, and/or any other relevant parameters or factors monitored or otherwise provided or programmed in the system 100 (FIG. 1).

Figure 7:
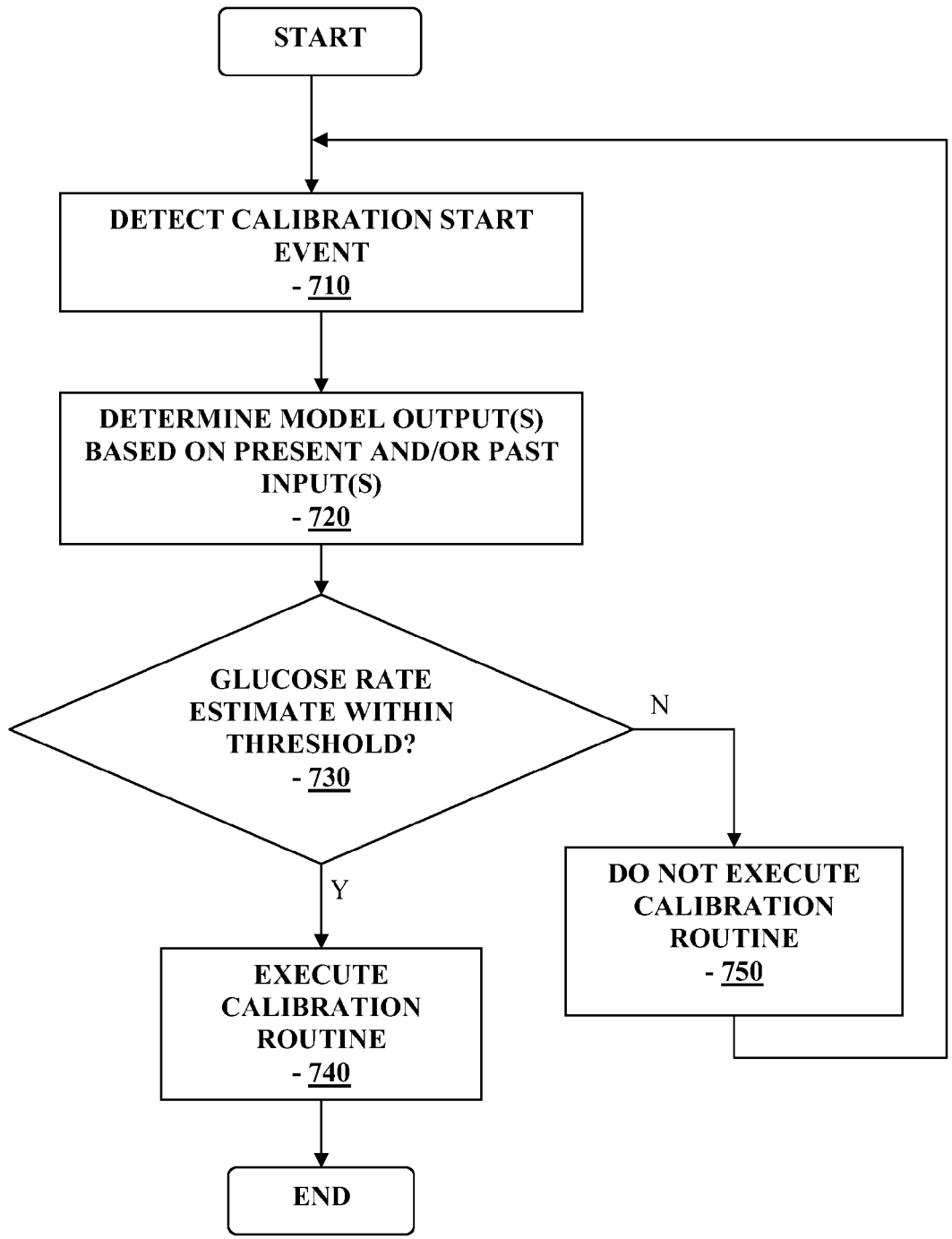
FIG. 7 is a flowchart illustrating calibration accuracy improvement routine in another aspect of the present disclosure.

Referring now again to the Figures, FIG. 7 is a flowchart illustrating calibration accuracy improvement routine in another aspect of the present disclosure. Referring to FIG. 7, in the embodiment shown, when the calibration start event is detected at step 710 the routine determines one or more physiological model outputs based on one or more present and/or past input parameters and values (720) including, for example, monitored sensor data, insulin delivery information, blood glucose estimates, blood glucose rate of change estimate values, and the like. Thereafter, at step 730, it is determined whether the rate of change of the estimated glucose level deviates from a predetermined threshold (for example, where the estimated rate exceeds a preset positive value, or the estimated rate falls below a preset negative value). If it is determined that the estimated glucose rate of change is not within the predetermined threshold at step 730, then at step 750, the routine discontinues the calibration function (or postpones or delays the initiated calibration routine). Thereafter, as shown in FIG. 7, the routine returns to the beginning to detect the subsequent calibration start event at step 710.

Referring still to FIG. 7, if at step 730 it is determined that the estimated glucose rate of change is within the predetermined threshold, then at step 740, the routine proceeds with the execution of the calibration routine to determine, for example, the sensitivity associated with the analyte sensor by prompting the user to input a reference blood glucose measurement value (for example, based on an in vitro blood glucose testing), or the system may be configured to retrieve an existing or contemporaneously received reference measurement data to determine the sensitivity value for calibrating the sensor data.

Figure 8:
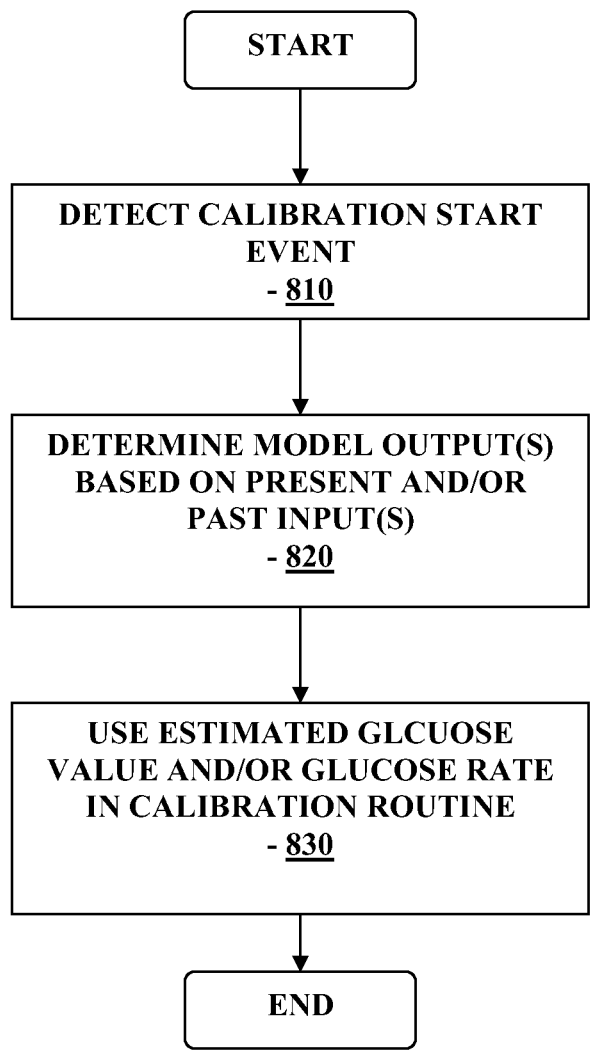
FIG. 8 is a flowchart illustrating calibration accuracy improvement routine in another aspect of the present disclosure.

FIG. 8 is a flowchart illustrating calibration accuracy improvement routine in another aspect of the present disclosure. Referring now to FIG. 8, when the calibration start event is detected at step 810 and the model outputs are determined based on one or more present and/or past input parameters or values (820) as discussed above in conjunction with FIG. 7, in the embodiment shown in FIG. 8, the calibration routine is executed based, in part on the estimated glucose value and/or the determined rate of change of the glucose level (830). That is, in one embodiment, when the scheduled calibration routine is initiated, the routine determines the most suitable or accurate parameters or values that are available to proceed with the execution of the calibration routine (as compared to determining whether or not the calibration condition is appropriate).

Figure 9:
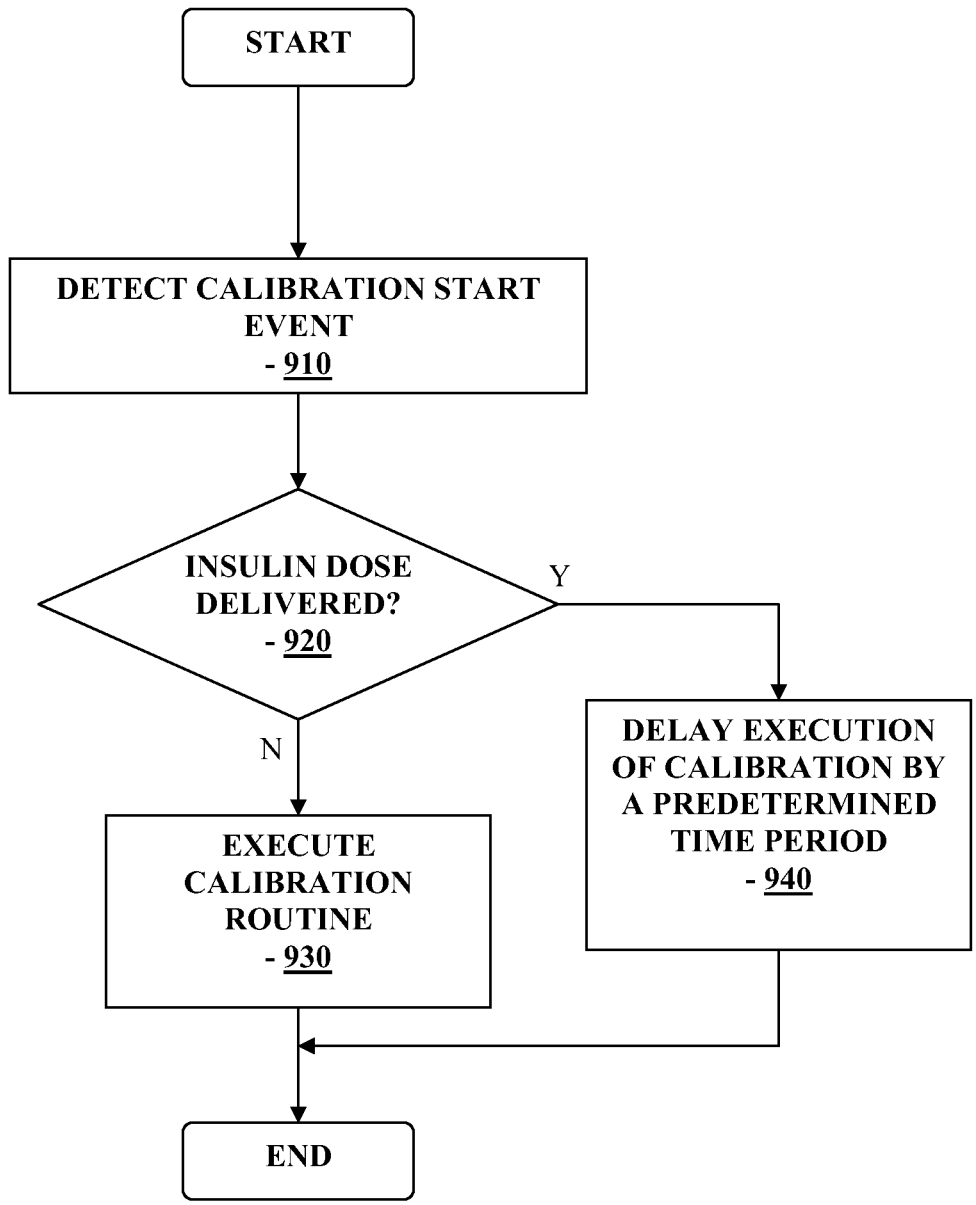
FIG. 9 is a flowchart illustrating calibration accuracy improvement routine in another aspect of the present disclosure.

FIG. 9 is a flowchart illustrating calibration accuracy improvement routine in another aspect of the present disclosure. Referring to FIG. 9, in one aspect, when the calibration start event is detected at step 910, it is thereafter determined when an insulin dose has been delivered at step 920. That is, when a scheduled calibration routine is called or initiated, the routine determines whether there has been insulin dose delivery that may impact the conditions associated with the calibration of the analyte sensor. For example, in one aspect, the routine may determine whether the insulin dose is delivered within a predetermined time period measured from the initiation of the calibration routine (step 910) such as, within the past 1-2 hours, for example. That is, the system may be configured such that insulin dose administered outside such predetermined time period may be considered not sufficiently significant to adversely affect the conditions related to the calibration of the analyte sensor, and therefore, ignored.

Referring again to FIG. 9, when it is determined that the insulin dose was delivered (920) for example, during the relevant predetermined time period, the scheduled calibration function is delayed for a predetermined or programmed time period. That is, the scheduled calibration function is executed after the programmed time period has expired at step 940 (such that any potentially adverse affect of the detected insulin dose delivery (at step 920) has dissipated sufficiently during the programmed time period to proceed with the calibration routine). On the other hand, if it is determined that there is no insulin dose delivery detected (920) or any detected insulin dose delivery falls outside the relevant time period, then at step 930, the initiated calibration routine is performed as described above. In this manner, in one aspect of the present disclosure, when insulin dose administration such as bolus dose administration is detected within a relevant time period during a scheduled or user initiated calibration routine, a time delay function is provided to dissipate the effects of the administered insulin dose, before calibration routine resumes.

Figure 10:
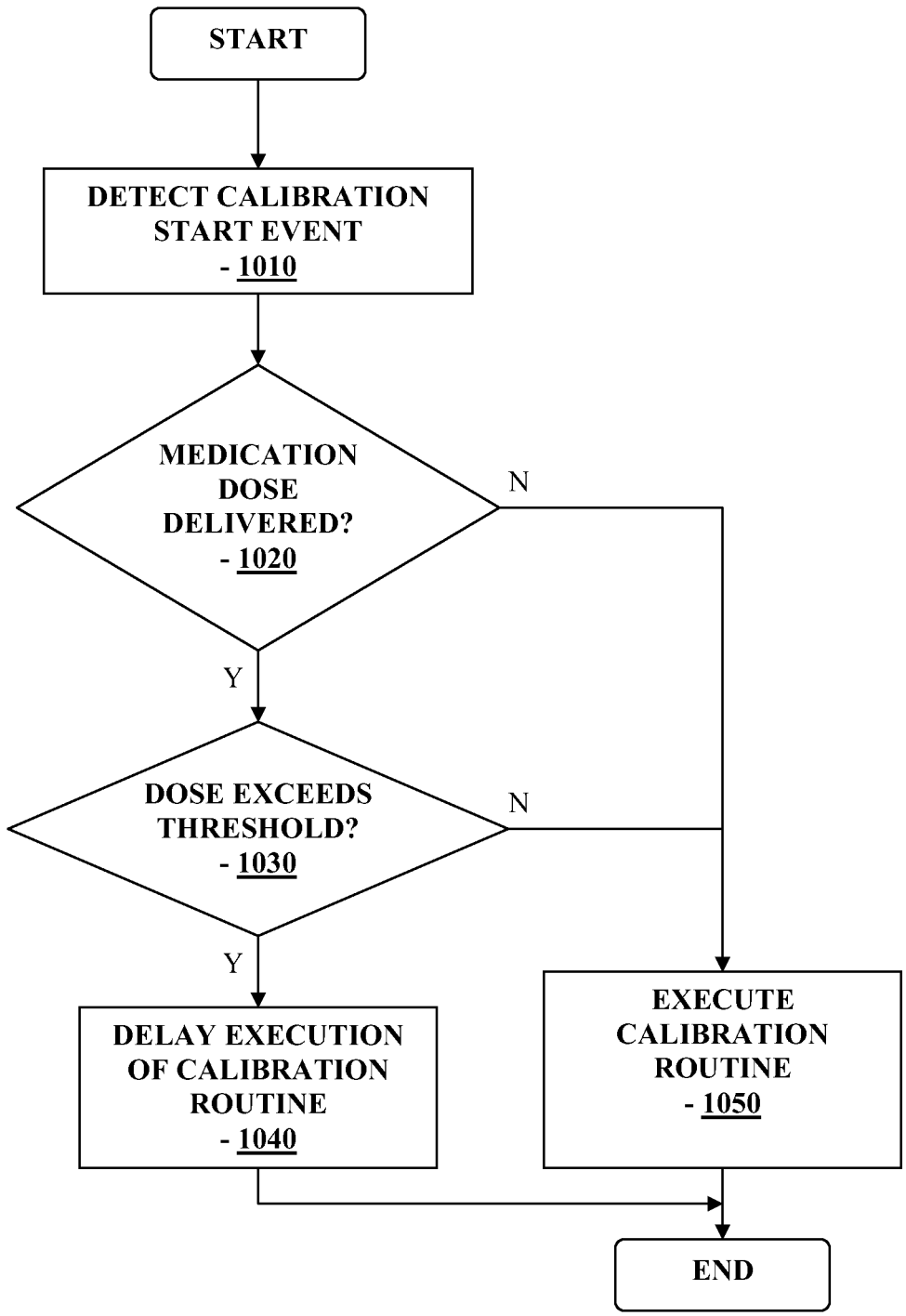
FIG. 10 is a flowchart illustrating calibration accuracy improvement routine in another aspect of the present disclosure.

FIG. 10 is a flowchart illustrating calibration accuracy improvement routine in another aspect of the present disclosure. Referring to FIG. 10, in the embodiment shown, upon detection of the calibration start event 1010, it is determined whether a medication dose (such as insulin dose) was delivered (1020) (for example, during a relevant time period as described above in conjunction with FIG. 9 above). If not, then the calibration routine is executed to completion at step 1050. On the other hand, if it is determined that the medication dose was delivered during the relevant time period (1020) (for example, within 1-2 hours of the detected calibration start event), at step 1030, the amount of delivered medication dose is compared against a threshold level to determine whether the delivered medication dose exceeds the threshold level. If not, then the calibration routine is executed or performed to completion as described above at step 1050.

If on the other hand it is determined that the delivered medication dose exceeds the threshold level, then at step 1040, the detected start of the calibration event is delayed or postponed for a preprogrammed time period. In one aspect, the preprogrammed time period may be dynamically adjusted based on the amount of the medication dose that exceeds that threshold level, or alternatively, the preprogrammed time period may be a fixed value. In this manner, in one aspect, when it is determined that medication dose was administered contemporaneous to a scheduled calibration event, the routine may be configured to determine the relevance of the delivered medication dose to modify the calibration timing accordingly (for example, to continue with the execution of the calibration routine or to delay the calibration routine to minimize any potential adverse effect of the delivered medication dose).

Figure 11:
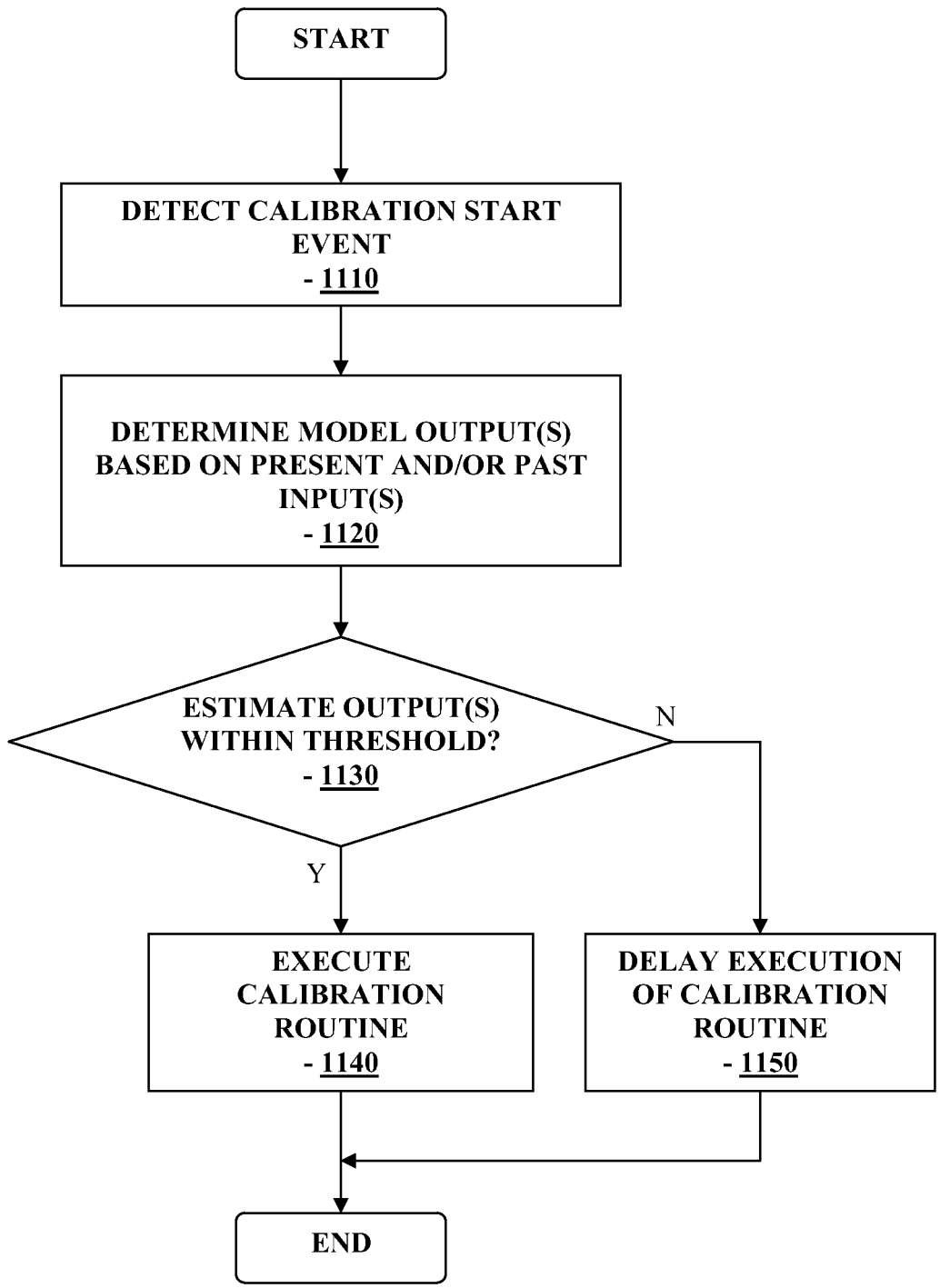
FIG. 11 is a flowchart illustrating calibration accuracy improvement routine in another aspect of the present disclosure.

FIG. 11 is a flowchart illustrating calibration accuracy improvement routine in another aspect of the present disclosure. Referring to FIG. 11, in the embodiment shown, when the calibration start event is detected 1110, a model based on one or more output values is determined based on one or more present and/or past input parameters or values (1120) as discussed above in conjunction with FIGS. 7 and 8 above, for example. It is to be noted that the model based determination as described herein may include one or more physiological models determined to a particular individual, condition and/or the severity of the condition or customized for one or more specific applications.

Referring to FIG. 11, after the model based outputs are determined at step 1120, it its determined whether the determined outputs or estimates of the outputs are within a predetermined threshold level at step 1130. That is, output parameters or values are determined based on one or more predetermined model applications relevant to, for example, the glycemic profile of a patient or a type of patients, and thereafter, the determined or estimated output parameters are compared to the predetermined threshold level. When it is determined that the estimated outputs are not within the threshold level, then at step 1150, the initiated calibration routine is delayed or postponed for a predetermined time period before executing the calibration function to completion as described above.

On the other hand, as shown in FIG. 11, if it is determined that the estimated output parameters or values are within the predetermined threshold value, the at step 1140, the calibration routine is executed, for example, to determine the sensitivity associated with the analyte sensor based on available reference glucose data, and thereafter calibrating the sensor data.

As discussed, in aspects of the present disclosure, the calibration accuracy routines may include other parameters or data such as, for example, meal intake information. For example, an aspect of the calibration routine may include confirming or determining whether a meal event has occurred for example, within the last hour prior to the scheduled calibration event, and further postpone or delay calibration if it is determined that the consumed meal during the past hour was sufficiently large or greater than a set threshold amount (for example, based on carbohydrate estimate). In one aspect, the meal intake information parameter used in conjunction with the calibration routine may be performed in conjunction with the insulin dose information as described above, or alternatively, as a separate routine for determining or improving the timing of performing the calibration routines.

In another aspect, the insulin dose information and/or other appropriate or suitable exogenous data/information may be used to improve the sensor sensitivity determination. For example, in one aspect, a model may be used to account for blood glucose and interstitial glucose, and insulin measurement data is used to help compensate for the lag between the two. The model would produce a blood glucose estimate that could be related to the reference blood glucose estimate in order to determine the sensitivity. Alternatively, the sensitivity could be part of the model and estimated. Additional detailed description related to pump information to improve analyte sensor accuracy is provided in U.S. patent application Ser. No. 12/024,101 entitled "Method and System for Determining Analyte Levels", the disclosure of which is incorporated by reference for all purposes.

More specifically, referring back to and based on an example of the blood-to-interstitial glucose dynamics model which accounts for insulin, an estimated sensitivity at time $t_0$ that is a function of available reference blood glucose (BG)

measurement, analyte sensor measurement, and insulin information can be described as below:

$$\hat{S}(t_o) = \frac{[\hat{y}_{CGM}(t_o) + [k_{02}\ y_{CGM}(t_o)]] + F_{02}}{[k_{21} + [k_i[I(t_o) - I_b]]]y_{BG}(t_o)} \quad (5)$$

It is to be noted that if insulin information is not accounted for, as shown in Equation 5 above, the denominator will be smaller, resulting in the sensitivity estimate larger than the actual value.

In another aspect, a closed loop control system is contemplated where a portion of the control algorithm seeks not only to prevent glucose excursions outside the euglycemic range, but also to provide improved conditions for calibration. While two particular conditions are described as examples, within the scope of the present disclosure, other conditions may be contemplated that are suitable or appropriate, depending on the type of analyte sensor used and/or other factors, variables or parameters.

In some cases, two conditions or states generally provide better calibration performance (i.e., better accuracy in sensitivity estimate)—calibrating during higher glucose periods and during low glucose rates-of-change. Calibrating during high glucose episodes is favorable because some errors tend to be unrelated to glucose level and will contribute to the sensitivity calculation proportionally less when glucose is high. In addition, as discussed above, error induced due to lag between blood glucose and interstitial glucose is minimized when glucose rate-of-change is low.

Figure 12:
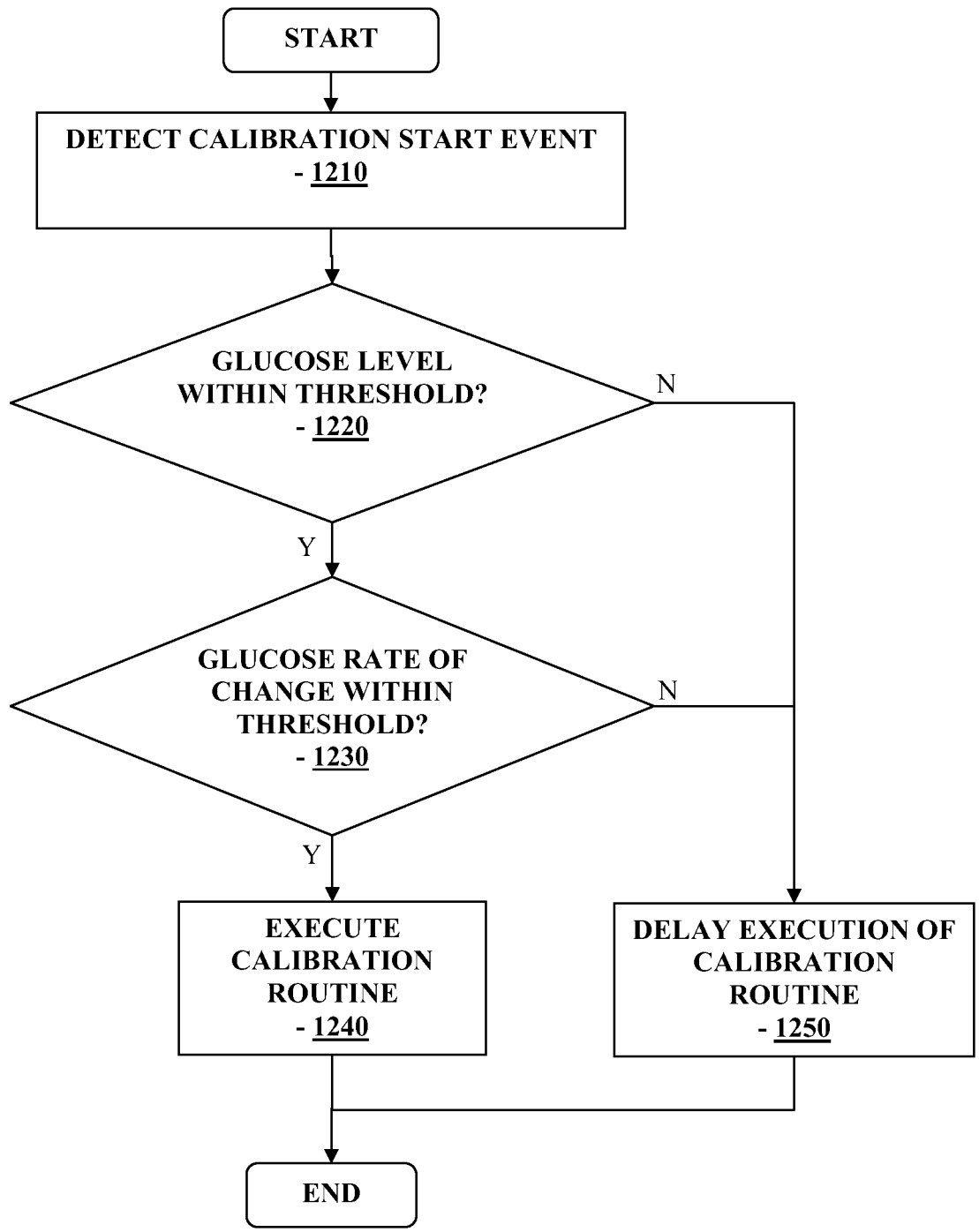
FIG. 12 is a flowchart illustrating calibration accuracy improvement routine in another aspect of the present disclosure.

FIG. 12 is a flowchart illustrating calibration accuracy improvement routine in another aspect of the present disclosure. Referring to FIG. 12, in the embodiment shown, when the calibration start event is detected (1210), it is determined whether the current or an anticipated or estimated glucose level is within a predetermined threshold level (1220). In certain embodiments, the threshold level is a higher than average glucose level. As described above, a higher than average glucose level may be favorable in certain embodiments for calibration because some errors may be proportionally less when the glucose level is high. In one aspect, if it is determined that the glucose level is not within the predetermined threshold, then the initiated calibration routine is not contemporaneously executed, but rather, the scheduled calibration function is delayed for a predetermined or programmed time period (1250).

Referring still to FIG. 12, if it is determined that the glucose level is within the predetermined threshold at step 1220, it is then determined whether the glucose rate-of-change is within a predetermined threshold (1230). In certain embodiments, as described above, performing calibration when the glucose level is fluctuating at a low rate-of-change may minimize errors, for example, due to lag between blood glucose and interstitial glucose levels. In one aspect, if it is determined that the glucose rate-of-change is not within the predetermined threshold, then the initiated calibration routine is not contemporaneously executed, but rather, the scheduled calibration function is delayed for a predetermined or programmed time period (1250). On the other hand, if the rate-of-change is within the threshold then the calibration routine is executed or performed to completion as described above at step 1240. In other embodiments, the calibration routine may be executed if only one of the glucose level and the rate-of-change of the glucose level are within the corresponding threshold levels.

Figure 13:
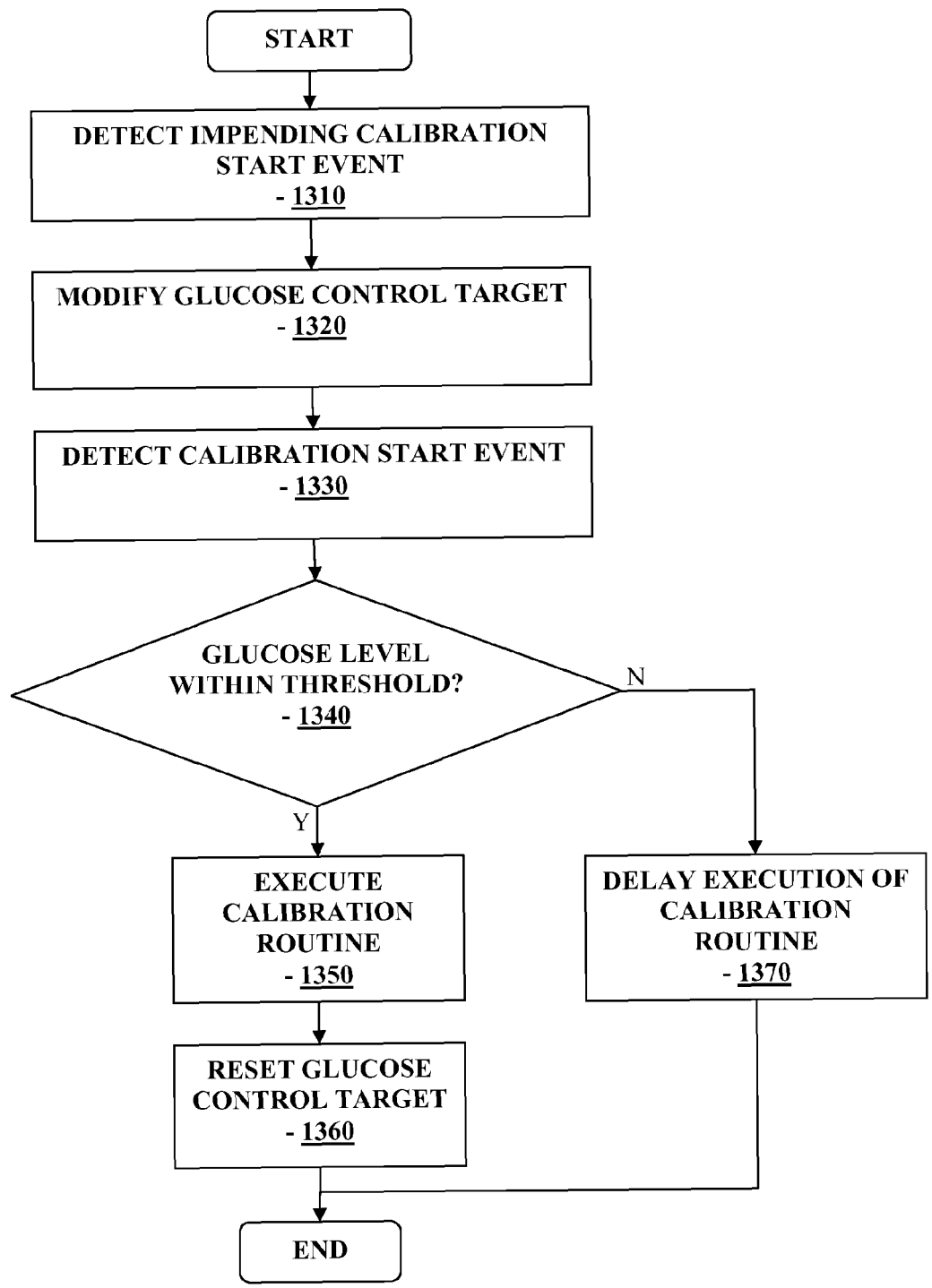
FIG. 13 is a flowchart illustrating calibration accuracy improvement routine in another aspect of the present disclosure.

FIG. 13 is a flowchart illustrating calibration accuracy improvement routine in another aspect of the present disclosure. Referring to FIG. 13, in one aspect of the present disclosure, the calibration routine may be configured to notify or inform the closed-loop control process or algorithm that calibration is required (or soon to be required) (1310). It should be noted that calibration routine may also be requested or initiated by the patient or the caregiver (e.g., health care provider (HCP)). Upon detection or determination of an impending calibration start event (1310), whether by user initiation or automatic initiation (i.e. at a predetermined time interval or in response to an event), the closed-loop control routine may be configured to modify the glucose control target to a higher value (1320) (balancing with a value that may be too high as to be detrimental to the patient).

Referring again to FIG. 13, once the calibration start event is detected (1330) the calibration routine, using the modified glucose control target, may be configured to determine if the current glucose level is within a target threshold, such as the target set by the modified glucose control target (1340) and only request or execute the calibration function (1350) if the glucose level is within the target threshold. If it is determined that the glucose level is not within the predetermined threshold, then the initiated calibration routine is not contemporaneously executed, but rather, the calibration function is delayed for a predetermined or programmed time period (1370). At this point, in certain embodiments, the routing may wait a predetermined amount of time and then the routine is restarted. Once the calibration function is executed (1350), the glucose control target may be reset back to normal glucose control target settings (1360).

In addition, the closed-loop control routine in one aspect may be configured to switch to a control target of maintaining a low rate of change of glucose, where the control target may be configured to incorporate the desired glucose threshold or range.

In one embodiment, control algorithm may be programmed or configured to maintain multiple control targets for optimal calibration glucose profile and euglycemic management. In one aspect, euglycemic management is configured as a higher priority over optimal calibration profile for the safety of the patient, in the control algorithm.

In the case where a model-based control algorithm is implemented, a vector of state estimates x(t) are provided that accounts for plasma insulin, plasma glucose, and other relevant states, the state observer may be realized in the form of a Kalman Filter or other types of state observers, and configured to use the analyte sensor data as its source of measurement, in addition to the insulin delivery or dosing information. One example of a model-based control algorithm includes a Linear Quadratic (LQ) controller, where the objective function governs the tradeoff between minimizing tracking error and maximizing control effort efficiency. Then, the relative weights under normal operation and when calibration is near can be appropriately adjusted or modified.

For example, consider the following truth model:

$\dot{I}_1(t) = -k_a I_1(t) + u_{sc}(t)$ $\dot{I}_2(t) = -k_a I_2(t) + k_a I_1(t)$ $\dot{I}(t) = -k_e I(t) + k_a/V I_2(t)$ $\dot{r}_1(t) = -k_{b1} r_1(t) + k_{a1} I(t)$ $\dot{r}_2(t) = -k_{b2} r_2(t) + k_{a2} I(t)$ $\dot{r}_3(t) = -k_{b3} r_3(t) + k_{a3} I(t)$ $$\dot{g}_b(t) = -[r_1(t)+k_{31}]g_b(t) - F_R + k_{12}g_i(t) + k_{13}g_2(t) + EGP(r_3) + g_m(t)$$

$$\dot{g}_2(t) = -[r_2(t)+k_{13}]g_2 + r_1(t)g_b(t)$$

$$\dot{g}_i(t) = -k_{02}g_i(t) + [k_{21}+[k_i[I(t)-I_b]]]g_b(t) - F_{02} \quad (6)$$

where, in addition to Equations 1 and 2 above, other glucose compartments $g_b$ and $g_2$ as well as effective insulin compartments $r_1$, $r_2$, and $r_3$ have been included. In the case where the model for the control algorithm is configured to perform a local linearization at every time step:

$$\dot{x}(t) = A(t)x(t) + Bu(t) \quad (7)$$

$$u(t) = u_{sc}(t)$$

$$y(t) = y_{CGM}(t) = S[g_i(t) + v_i(t)]$$

$$x(t) = \begin{bmatrix} I_1 - I_{1t} \\ I_2 - I_{2t} \\ I_3 - I_{3t} \\ r_1 - r_{1t} \\ r_2 - r_{2t} \\ r_3 - r_{3t} \\ g_b - g_{bt} \\ g_2 - g_{2t} \\ g_i - g_{it} \end{bmatrix}$$

It is to be noted that the states have been defined as the difference between the physiologically meaningful states of the truth model and their corresponding targets.

Further, an LQ optimal control is determined such that the objective function J is minimized:

$$J = \int_t^{t+t_p} [[x^T(t)Qx(t)] + [u^T(t)Ru(t)]] dt \quad (8)$$

$$Q = \begin{bmatrix} q_{1,1} & \cdots & q_{1,9} \\ \vdots & \ddots & \vdots \\ q_{9,1} & \cdots & q_{9,9} \end{bmatrix}, \quad R = [r_{sc}]$$

where $t_p$ is a finite future horizon in which the controller must be optimized for, Q is a positive semidefinite matrix that penalizes linear combinations of the states x, and R is a positive definite matrix that penalizes the control action.

In particular, the distinction between controlling for optimal calibration and controlling for optimal glucose regulation, using this LQ framework as an example, is described below. In the case of controlling for optimal glucose regulation, for a given desired strict plasma glucose target of 100 mg/dL, the quantity $g_{bt}$ is set to 100 mg/dL, so that when the objective function in Equation 8 is evaluated, any deviation of $g_b$ from this value will contribute to an increase in J.

If other states do not need to be regulated at any specific level, then the corresponding targets $I_{1t}$, $I_{2t}$, and so on, can be set to any arbitrary real value (such as zero), and Q must be tuned such that only $q_{7,7}$ (which corresponds to the penalty for $g_b$) be left nonzero. The relative magnitude between $q_{7,7}$ and $r_{sc}$ then determines aggressive target tracking and conservative control action.

In the case of controlling for optimal calibration, a combination of strict plasma glucose target and zero glucose rate is obtained, which, in one aspect may be approximated by setting the rate of change of the glucose rates to zero. As a result, the corresponding targets for the glucose compartments can be estimated as follows:

$$\begin{bmatrix} g_{bt} \\ g_{2t} \\ g_{it} \end{bmatrix} = \quad (9)$$

$$\text{inv}\left(\begin{bmatrix} -[r_1+k_{31}] & k_{13} & k_{12} \\ r_1 & -[r_2+k_{13}] & 0 \\ k_{21}+[k_i[I-I_b]] & 0 & k_{02} \end{bmatrix}\right)\begin{bmatrix} F_R - EGP(r_3) - g_m \\ 0 \\ F_{02} \end{bmatrix}$$

The above targets can be assigned to the glucose compartments, and as in the optimal glucose regulation case, other targets can be set to zero. The proper state weighting matrix Q must be set such that the glucose states track the established targets.

If calibration favors not only steady glucose but also a particular blood glucose value, then the target for blood glucose may be set explicitly (e.g. $g_{bt}$=100 mg/dL), and the other glucose targets can be derived such that the following is satisfied:

$$\begin{bmatrix} k_{13} & k_{12} \\ -[r_2+k_{13}] & 0 \\ 0 & -k_{02} \end{bmatrix}\begin{bmatrix} g_2 \\ g_i \end{bmatrix} = \begin{bmatrix} F_R - EGP(r_3) - g_m + [r_1+k_{31}]g_{bt} \\ -r_1 g_{bt} \\ F_{02} - [k_{21}+[k_i[I-I_b]]]g_{bt} \end{bmatrix} \quad (10)$$

The targets for $g_2$ and $g_i$ can then be computed using the least-squares error approximation shown:

$$\begin{bmatrix} g_{2t} \\ g_{it} \end{bmatrix} = \text{inv}\left(\begin{bmatrix} k_{13} & -[r_2+k_{13}] & 0 \\ k_{12} & 0 & -k_{02} \end{bmatrix}\begin{bmatrix} k_{13} & k_{12} \\ -[r_2+k_{13}] & 0 \\ 0 & -k_{02} \end{bmatrix}\right) \quad (11)$$

$$\begin{bmatrix} k_{13} & -[r_2+k_{13}] & 0 \\ k_{12} & 0 & -k_{02} \end{bmatrix}\begin{bmatrix} F_R - EGP(r_3) - g_m + [r_1+k_{31}]g_{bt} \\ -r_1 g_{bt} \\ F_{02} - [k_{21}+[k_i[I-I_b]]]g_{bt} \end{bmatrix}$$

In the manner described above, in accordance with aspects of the present disclosure, one or more parameters or information of events that may impact the level of blood glucose or glucose measurements, if available during the analyte sensor calibration process, may be factored in to improve the sensor calibration accuracy, for example, by improving the accuracy of the sensor sensitivity determination. Events or conditions referred to herein include, but not limited to exercise information, meal intake information, patient health information, medication information, disease information, physiological profile information, and insulin delivery information. While the various embodiments described above in conjunction with the improvement of the sensor calibration accuracy include insulin delivery information, within the scope of the present disclosure, any exogenous information that are available to the and during the calibration process or routine that may have an impact on the level of glucose may be considered.

In one aspect, the user or the patient may provide this information into one or more components of the system 100 (FIG. 1) which includes a user interface for entering events and/or data. Alternatively, this information may be entered manually into another device and transferred electronically to the processor(s) performing the calibration process/routine.

Finally, this information may be recorded by either the device(s) that perform the calibration process/routine, or by a separate device that transfers the information electronically to the device(s) that perform the calibration process/routine.

In one embodiment, the medication delivery device is configured to deliver appropriate medication based on one or more delivery profiles stored therein, and in addition, configured to record the amount of medication delivered with delivery time association in an electronic log or database. The medication delivery device may be configured to periodically (automatically, or in response to one or more commands from the controller/another device) transfer medication delivery data/information to the controller (or another device) electronic log or database. In this manner, the analyte monitoring device including the receiver/controller unit may be provided with software programming that can be executed to perform the sensor calibration routine and provided with access to all relevant information received from the medication delivery unit, the analyte sensor/transmitter, user input information, as well as previously stored information.

In this manner, in one aspect of the present disclosure, the accuracy of the sensor sensitivity determination may be improved based on the insulin delivery information which provides additional data to determine or anticipate future glucose values, and may help to compensate for potential error in the sensor readings or measurements due to lag, in particular, when the level of glucose is undergoing a rapid fluctuation. In addition, the insulin information may be used to adjust or determine the suitable or appropriate time to perform the sensor calibration routine. For example, this information may be used to determine or anticipate periods of high rates of glucose change which would not be an ideal condition for determining sensor sensitivity for performing sensor calibration.

Within the scope of the present disclosure, the programming, instructions or software for performing the calibration routine, user interaction, data processing and/or communication may be incorporated in the analyte monitoring device, the medication delivery device, the control unit, or any other component of the overall system 100 shown in FIG. 1, and further, may also be provided in multiple devices or components to provide redundancy. Additionally, embodiments described herein may also be integrated in a closed loop control system which is programmed to control insulin delivery so as to provide, in part, conditions that are suitable for performing sensor calibration in the closed loop control system.

In one embodiment, a method may include detecting an analyte sensor calibration start event, determining one or more parameters associated with a calibration routine corresponding to the detected calibration start event, and executing the calibration routine based on the one or more determined parameters, wherein the one or more determined parameters includes a medication delivery information.

Detecting the calibration start event may include monitoring an elapsed time period from initial analyte sensor placement.

Detecting the calibration start event may be based at least in part on a predetermined schedule.

The predetermined schedule may include approximately once every twenty four hours.

The determined one or more parameters may include an amount of insulin dose delivered, a time period of the delivered insulin dose, an insulin sensitivity parameter, an insulin on board information, an exercise information, a meal intake information, an activity information, or one or more combinations thereof.

The medication delivery information may include an insulin delivery amount and time information relative to the detected calibration start event.

Executing the calibration routine may include delaying the calibration routine by a predetermined time period.

The predetermined time period may include approximately 1-2 hours.

The calibration routine may not be executed when one of the one or more determined parameters deviates from a predetermined threshold level.

The predetermined threshold level may be dynamically modified based on a variation in the corresponding one or more determined parameters.

The predetermined threshold level may be user defined.

Executing the calibration routine may include determining a reference measurement value.

Determining the reference measurement value may include prompting for a blood glucose measurement, and receiving data corresponding to the measured blood glucose level.

Executing the calibration routine may include determining a sensitivity value associated with the analyte sensor.

Executing the calibration routine may include calibrating the analyte sensor.

In another embodiment, a device may include one or more processors and a memory operatively coupled to the one or more processors, the memory for storing instructions which, when executed by the one or more processors, causes the one or more processors to detect an analyte sensor calibration start event, to determine one or more parameters associated with a calibration routine corresponding to the detected calibration start event, and to execute the calibration routine based on the one or more determined parameters, wherein the one or more determined parameters includes a medication delivery information.

The analyte sensor may include a glucose sensor.

The medication delivery information may include information associated with insulin dose administered.

Furthermore, an output unit may be operatively coupled to the one or more processors for outputting one or more data or signals associated with the calibration start event or the calibration routine.

In yet another embodiment, a method may include initializing an analyte sensor, receiving a data stream from the initialized analyte sensor, detecting a calibration start event associated with the initialized analyte sensor, determining one or more parameters associated with insulin dose administration, and executing a calibration routine based on the one or more determined parameters.

In yet another embodiment, a method may include detecting an impending glucose sensor calibration start event, modifying a medical treatment profile to a higher than average target glucose level upon detection of the impending glucose sensor calibration start event, determining one or more parameters associated with a calibration routine corresponding to the detected impending calibration start event, wherein the one or more determined parameters includes a current glucose level, executing the calibration routine based on the one or more determined parameters, and resetting the medical treatment profile to an average target glucose level.

The calibration routine may be executed only if the current glucose level is above a predetermined threshold.

The predetermined threshold may be higher than the average glucose level.

In one aspect, the method may include delaying execution of the calibration routine until the current glucose level is above the predetermined threshold.

In another aspect, the method may include outputting one or more data or signals associated with the calibration routine.

The medical treatment profile may include insulin dose administration information.

Various other modifications and alterations in the structure and method of operation of this disclosure will be apparent to those skilled in the art without departing from the scope and spirit of the present disclosure. Although the present disclosure has been described in connection with specific embodiments, it should be understood that the present disclosure as claimed should not be unduly limited to such specific embodiments. It is intended that the following claims define the scope of the present disclosure and that structures and methods within the scope of these claims and their equivalents be covered thereby.

What is claimed is:

1. A method implemented using one or more processors, the method comprising:
   detecting a system check start event;
   determining one or more parameters associated with a system check routine corresponding to the detected system check start event; and
   executing the system check routine based on the one or more determined parameters;
   wherein the one or more determined parameters include a medication delivery information.

2. The method of claim 1, wherein detecting the system check start event includes monitoring an elapsed time period from an initial positioning of an analyte sensor.

3. The method of claim 1, wherein detecting the system check start event is based at least in part on a predetermined schedule.

4. The method of claim 3, wherein the predetermined schedule includes approximately once every twenty four hours.

5. The method of claim 1, wherein the determined one or more parameters includes an amount of insulin dose delivered, a time period of the delivered insulin dose, an insulin sensitivity parameter, an insulin on board information, an exercise information, a meal intake information, an activity information, or one or more combinations thereof.

6. The method of claim 1, wherein the medication delivery information includes an insulin delivery amount and time information relative to the detected system check start event.

7. The method of claim 1, wherein executing the system check routine includes delaying the system check routine by a predetermined time period.

8. The method of claim 7, wherein the predetermined time period includes approximately 1-2 hours.

9. The method of claim 1, wherein the system check routine is not executed when one of the one or more determined parameters deviates from a predetermined threshold level.

10. The method of claim 9, wherein the predetermined threshold level is dynamically modified based on a variation in the corresponding one or more determined parameters.

11. The method of claim 9, wherein the predetermined threshold level is user defined.

12. The method of claim 1, wherein executing the system check routine includes determining a reference measurement value.

13. The method of claim 12, wherein determining the reference measurement value includes:
   prompting for a blood glucose measurement; and
   receiving data corresponding to a measured blood glucose level.

14. The method of claim 1, wherein executing the system check routine includes determining a sensitivity value associated with the analyte sensor.

15. The method of claim 1, wherein executing the system check routine includes calibrating an analyte sensor.

16. A device, comprising:
   one or more processors; and
   a memory operatively coupled to the one or more processors, the memory for storing instructions which, when executed by the one or more processors, causes the one or more processors to detect a system check start event, to determine one or more parameters associated with a system check routine corresponding to the detected system check start event, and to execute the system check routine based on the one or more determined parameters, wherein the one or more determined parameters include a medication delivery information.

17. The device of claim 16, wherein the system check routine includes calibrating an analyte sensor.

18. The device of claim 16, wherein the medication delivery information includes information associated with insulin dose administered.

19. The device of claim 16, further including an output unit operatively coupled to the one or more processors for outputting one or more data or signals associated with the system check start event or the system check routine.

20. A method implemented using one or more processors, the method comprising:
   initializing an analyte sensor;
   receiving a data stream from the initialized analyte sensor;
   detecting a system check start event associated with the initialized analyte sensor;
   determining one or more parameters associated with insulin dose administration; and
   executing a system check routine based on the one or more determined parameters.

* * * * *